(12) United States Patent
Rush et al.

(10) Patent No.: US 7,744,653 B2
(45) Date of Patent: Jun. 29, 2010

(54) VACUUM PUMP WITH SHOCK ABSORPTION AND CONTROLLED ROTATION FOR PROSTHETIC DEVICES

(75) Inventors: Douglas E. Rush, Draper, UT (US); Nathan A. Williams, Heber City, UT (US); Robert Edward Finlinson, Salt Lake City, UT (US); Luder Mosler, Duderstadt (DE); Martin Hillmann, Duderstadt (DE); Richard Skiera, Vienna (AT)

(73) Assignee: Otto Bock HealthCare LP, Minneapolis, MN (US)

( * ) Notice: Subject to any disclaimer, the term of this patent is extended or adjusted under 35 U.S.C. 154(b) by 1246 days.

(21) Appl. No.: 11/112,352

(22) Filed: Apr. 22, 2005

(65) Prior Publication Data

US 2005/0240282 A1    Oct. 27, 2005

Related U.S. Application Data

(60) Provisional application No. 60/564,423, filed on Apr. 22, 2004.

(51) Int. Cl.
  *A61F 2/80* (2006.01)
(52) U.S. Cl. .............................. 623/34; 623/35; 623/36
(58) Field of Classification Search ............. 623/26–46
  See application file for complete search history.

(56) References Cited

U.S. PATENT DOCUMENTS

| 2,696,011 | A | 12/1954 | Galdik |
| 5,133,776 | A | 7/1992 | Crowder |
| 5,201,774 | A | 4/1993 | Greene |
| 5,258,037 | A | 11/1993 | Caspers |
| 5,458,656 | A | 10/1995 | Phillips |
| 5,658,353 | A | 8/1997 | Layton |
| 5,702,489 | A | 12/1997 | Slemker |

(Continued)

FOREIGN PATENT DOCUMENTS

CA    2574889    2/2006

(Continued)

OTHER PUBLICATIONS

Product Information: Otto Bock Delta Twist Shock Absorber, printed Apr. 22, 2004, 2 pages.

(Continued)

*Primary Examiner*—Bruce E Snow
(74) *Attorney, Agent, or Firm*—Faegre & Benson LLP

(57) ABSTRACT

A vacuum pump having shock absorption and controlled rotation for use in an artificial limb. The pump includes a housing having a first chamber, and a shaft configured to be received by and to reciprocate within the first chamber, the housing and shaft forming a pump chamber. A piston may be coupled to the shaft and positioned within the pump chamber, and intake and exhaust ports are fluidly coupled to the pump chamber. Rotational structure is mounted with respect to the pump to provide controlled rotation of the shaft relative to the housing, and shock absorption structure is included within the pump to provide shock absorption for the shaft. Both a pneumatic spring and a mechanical spring element may be provided for the shock absorption structure. An optional adapter couples the shaft to the pylon of an integral pylon prosthetic foot.

21 Claims, 32 Drawing Sheets

U.S. PATENT DOCUMENTS

| | | |
|---|---|---|
| 5,800,562 A | 9/1998 | Wilkinson |
| 5,888,214 A | 3/1999 | Ochoa |
| 5,904,721 A | 5/1999 | Henry et al. |
| 6,004,116 A | 12/1999 | Wang |
| 6,063,125 A | 5/2000 | Arbogast et al. |
| D429,335 S | 8/2000 | Caspers et al. |
| 6,117,177 A | 9/2000 | Chen et al. |
| 6,287,345 B1 | 9/2001 | Slemker et al. |
| 6,302,918 B1 | 10/2001 | Gramnas |
| 6,395,039 B1 | 5/2002 | Thorn |
| 6,468,315 B1 | 10/2002 | Wilkinson et al. |
| 6,478,826 B1 | 11/2002 | Phillips et al. |
| 6,511,512 B2 | 1/2003 | Phillips et al. |
| 6,554,868 B1 | 4/2003 | Caspers |
| 6,645,253 B2 | 11/2003 | Caspers |
| 6,682,569 B2 | 1/2004 | Wilkinson et al. |
| 6,761,742 B2 | 7/2004 | Caspers |
| 6,827,343 B2 | 12/2004 | Skiera |
| 6,877,965 B2 | 4/2005 | McCall et al. |
| 6,887,279 B2 | 5/2005 | Phillips et al. |
| 6,926,742 B2 | 8/2005 | Caspers et al. |
| 6,969,408 B2 | 11/2005 | Lecomte et al. |
| 7,025,792 B2 | 4/2006 | Collier |
| 7,169,190 B2 | 1/2007 | Phillips et al. |
| 7,228,923 B2 | 6/2007 | Takenaka et al. |
| 7,371,262 B2 | 5/2008 | Lecomte et al. |
| 2001/0016781 A1 | 8/2001 | Caspers |
| 2003/0191539 A1* | 10/2003 | Caspers .................. 623/35 |
| 2004/0143345 A1 | 7/2004 | Caspers |
| 2004/0181290 A1 | 9/2004 | Caspers |
| 2005/0131511 A1 | 6/2005 | Westlund |
| 2005/0197611 A1 | 9/2005 | Taranow |
| 2005/0240282 A1 | 10/2005 | Rush et al. |
| 2006/0212130 A1 | 9/2006 | Collier |
| 2007/0196222 A1 | 8/2007 | Mosler et al. |
| 2009/0299491 A1 | 12/2009 | Slemker et al. |

FOREIGN PATENT DOCUMENTS

| | | |
|---|---|---|
| DE | 27 29 800 | 1/1979 |
| WO | WO84/00881 | 3/1984 |
| WO | WO01/70147 | 9/2001 |
| WO | WO 2006/012820 | 2/2006 |
| WO | WO 2009/015896 | 2/2009 |

OTHER PUBLICATIONS

"4R146=RPA Harmony® DP Instructions for Use", Otto Bock® HealthCare product brochure at www.ottobock.com, dated Dec. 2004, 1 pg.

"Harmony P2 and Hannony HD—Introducing the New Hannony® P2 from Otto Bock®:", product brochure at www.ottobock.com, dated 2004, 2 pgs.

"Harmony® 4R133, 4R134, 4R135, 4R144, 4R150 Instructions for Use", Otto Bock® HealthCare product brochure at www.ottobock.com, dated Mar. 2004, 13 pages.

"Harmony® Restoring Human Independence", Otto Bock® Healthcare product brochure at www.ottobock.com, dated Sep. 2004, 2 pages.

"The Harmony® Volume Management System Component Selection Chart", Otto Bock® product brochure at www.ottobock.com, dated Mar. 2005, 1 pg.

Beil, Tracy L., et al., "Interface pressures during ambulation using suction and vacuum-assisted prosthetic sockets", Department of Veterans Affairs, *Journal of Rehabilitation Research and Development*, vol. 39, No. 6, Nov./Dec. 2002, pp. 693-700.

Board, W.J. et al., "A Comparison of trans-tibial amputee suction and vacuum socket conditions", *Prosthetics and Orthotics International*, 2001, 25, pp. 202-209.

Goswami, J. et al., "Walking in a vacuum-assisted socket shifts the stump fluid balance", *Prosthetics and Orthotics International*, 2003, 23, pp. 107-113.

* cited by examiner dd# VACUUM PUMP WITH SHOCK ABSORPTION AND CONTROLLED ROTATION FOR PROSTHETIC DEVICES The present application claims the benefit of provisional patent application Ser. No. 60/564,423, entitled VACUUM PUMP WITH SHOCK ABSORPTION AND CONTROLLED ROTATION FOR PROSTHETIC DEVICES, filed on Apr. 22, 2004, and herein incorporated by reference in its entirety.

TECHNICAL FIELD

The present invention is related to vacuum pumps usable in prosthetic devices, such as artificial legs or arms. In particular, it is related to vacuum pumps including shock absorption and torsion.

BACKGROUND

An amputee is a person who has lost part of an extremity or limb such as a leg or arm, the remainder of which commonly may be termed as a residual limb. Residual limbs come in various sizes and shapes with respect to the stump. That is, most new amputations are either slightly bulbous or cylindrical in shape while older amputations that may have had a lot of atrophy are generally more conical in shape. Residual limbs may further be characterized by their various individual problems or configurations including the volume and shape of a stump and possible scar, skin graft, bony prominence, uneven limb volume, neuroma, pain, edema or soft tissue configurations.

Referring to FIG. 1, a below the knee residual limb 50 is shown and described as a leg 51 having been severed below the knee terminating in a stump 52. In this case, the residual limb 50 includes soft tissue as well as the femur 54, knee joint 55, and severed tibia 56 and fibula 57. Along these bone structures surrounded by soft tissue are nerve bundles and vascular routes which must be protected against external pressure to avoid neuromas, numbness and discomfort as well as other kinds of problems. A below the knee residual limb 50 has its stump 52 generally characterized as being a more bony structure while an above the knee residual limb may be characterized as including more soft tissue as well as the vascular routes and nerve bundles.

Referring to FIG. 2, amputees who have lost a part of their arm 60, which terminates in a stump 62 also may be characterized as having vascular routes, nerve bundles as well as soft and bony tissues. The residual limb 60 includes the humerus bone 64 which extends from below the shoulder 61 to the elbow 63 from which the radius 65 and ulna 66 bones may pivotally extend to the point of severance. Along the humerus bone 64 are the biceps muscle 67 and the triceps muscle 68 which still yet may be connected to the radius 65 and the ulna 66, respectively.

In some respects, the residual limb amputee that has a severed arm 60 does not have the pressure bearing considerations for an artificial limb but rather is concerned with having an artificial limb that is articulable to offer functions typical of a full arm, such as bending at the elbow and grasping capabilities. An individual who has a paralyzed limb would also have similar considerations wherein he or she would desire the paralyzed limb to having some degree of mobility and thus functionality.

Historically, artificial limbs typically used by a leg amputee were for the most part all made out of wood, such as an Upland Willow. The limbs were hand carved with sockets for receiving the stump 52 of the residual limb 50. Below the socket would be the shin portion with the foot below the shin. These wooden artificial limbs were covered with rawhide which often were painted. The sockets of most wood limbs were hollow as the limbs were typically supported in the artificial limb by the circumferential tissue adjacent the stump 52 rather than at the distal end of the stump 52.

Some artificial limbs in Europe were also made from forged pieces of metal that were hollow. Fiber artificial limbs were also used which were stretched around a mold after which they were permitted to dry and cure. Again, these artificial limbs were hollow and pretty much supported the residual limb about the circumferential tissue adjacent the stump 52.

All of these various artificial limbs have sockets into which the amputee's stump 52 is put. There are generally two categories of sockets. There are hard sockets wherein the stump 52 is placed into the socket and actually touches the socket wall without any type of liner or stump sock. Another category of sockets is a socket that utilizes a liner or insert. Both categories of sockets typically were open ended sockets having a hollow chamber in the bottom and no portion of the socket touched the distal end of the stump 52. So, the stump 52 was supported about its circumferential surface as it fit against the inside wall of the sockets.

These types of sockets caused a lot of shear force on the stump 52, as well as had pressure or restriction problems on the nerve bundles and vascular flow of fluid by way of the circumferential pressure effect of the socket on the limb. This pressure effect could cause a swelling into the ends of the socket where an amputee may develop severe edema and draining nodules at the end of their stump 52.

With time, it was learned that by filling in the socket's hollow chamber and encouraging a more total contact between the stump 52 and the socket, the swelling and edema problems could be eliminated. However, problematic tissue configurations, such as bony prominences, required special consideration, such as the addition of soft or pliable materials to be put into the socket.

Today, most artificial limbs are constructed from thermoplastics such as polyester resins, acrylic resins, polypropylenes and polyethylenes, which are often laminated over a nylon stockinette that also may be impregnated by the various resins.

In the past, most artificial limbs were suspended from the amputee's body by some form of pulley, belt or strap suspension often used with various harnesses and perhaps leather lacers or lacings. Another method of suspending artificial limbs is known as the wedge suspension wherein an actual wedge is built into the socket which is more closed at its top opening. The wedge in the socket cups a portion of the femur. Yet another form of suspension is referred to as the shuttle system, or a mechanical hookup or linkup wherein a thin suction liner is donned over the stump that has a docking device on the distal end which mechanically links up with its cooperative part in the bottom of the socket chamber. Sleeve suspensions were also used wherein the amputee may use a latex rubber tube which forms into a rubber-like sleeve which would be rolled on over both the top of the artificial limb and onto the amputee's thigh. The sleeve suspensions have been used in combination with other forms of suspensions techniques.

Both the use of a positive pressure system and the use of a negative pressure system (or a hypobaric closed chamber or a vacuum) have been utilized in the field of prosthetics. At one time, for positive pressure systems "inflatable inner tubes" were used to fit into sockets. Presently, there are pneumatic "bags" which are strategically placed over what people consider to be good weight-bearing areas to increase pressure to help accommodate for volume changes within the socket.

Some of the problems with these positive pressure systems are that they use a very specific pressure at specific locations resulting in the creation of atrophy and loss of tissue dramatically over these high pressure areas. None of these systems employs positive pressure distributed over the total contact area between the residual limb and the artificial limb socket to accommodate volume changes within the socket.

One system using negative pressure utilized a closed chamber with a socket that is donned by pulling on with a sock, pulling the sock out of the socket and then closing the opening with a valve. This creates a seal at the bottom and the stump is held into the socket by the hypobaric seal.

The older systems were initially started in Germany. They were an open-ended socket, meaning there was an air chamber in the bottom of the socket. This did not work particularly well because it would cause swelling of the residual limb into the chamber created by the negative draw of suspending the weight of the leg and being in a confined area. This would lead to significant edema which would be severe enough to cause stump breakdown and drainage.

It was later discovered in the United States that total contact is important between the residual limb and the socket to reduce uneven force distribution. Once total contact is achieved, the weight was distributed evenly or the suspension was distributed over the whole surface of the limb rather than just over the open chamber portion of the socket.

The human body as a whole is under approximately one atmosphere of pressure at sea level. It keeps and maintains a normal fluid system throughout the body. When an amputee dons a prosthesis and begins taking the pressures of transmitting the weight of the body through the surface area of the residual limb to the bone, there is increased pressure on the residual limb equal to one atmosphere plus whatever additional pressures are created by weight bearing. This increased pressure causes the eventual loss of fluids within the residual limb to the larger portion of the body which is under less pressure. This loss of fluids causes the volume of the residual limb to decrease during the day. It varies from amputee to amputee. The more "fleshy" and the softer the residual limb, the more volume fluctuation there will be. The greater the weight and the smaller the surface area, the greater the pressure will be and the more "swings" there will be in fluids. In the past, the amputee compensated for this volume decrease by removing the artificial limb and donning additional stump socks to make up for the decreased residual limb volume.

SUMMARY OF THE INVENTION

The present invention provides a vacuum pump having shock absorption and controlled rotation for use in an artificial limb. The vacuum pump includes a housing couplable to a first prosthetic structure, the housing including a first chamber; a shaft couplable to a second prosthetic structure and configured to be received by and to reciprocate within the first chamber, such that the housing and shaft together form a pump chamber; and an intake port and an exhaust port fluidly coupled to the pump chamber. The pump also includes a rotational structure mounted with respect to the pump and configured to control rotation of the shaft with respect to the housing, and a shock absorption structure included within the pump and configured to absorb a shock to the shaft upon movement into the pump and return of the shaft to an extended position relative to the housing. Stroke of the shaft within the pump chamber in a first direction results in expellation of gas out of the chamber through the exhaust valve, and stroke of the shaft in a second, opposite direction pulls gas into the pump chamber through the intake valve, which can create a vacuum in an external component coupled to the pump at the intake valve.

In an alternate embodiment, the present invention provides vacuum pump for use in an artificial limb including a prosthetic foot having an integral pylon. The vacuum pump includes a housing couplable to a prosthetic structure, the housing including a first chamber; a shaft configured to be received by and to reciprocate within the first chamber, with the housing and shaft together forming a pump chamber, and an intake port and an exhaust port fluidly coupled to the pump chamber. The shaft is adapted to receive and fasten a portion of the integral pylon of the prosthetic foot. Stroke of the shaft within the pump chamber in a first direction results in expellation of gas out of the chamber through the exhaust valve, and stroke of the shaft in a second, opposite direction pulls gas into the pump chamber through the intake valve, which can create a vacuum in an external component coupled to the pump at the intake valve.

DETAILED DESCRIPTION

Figure 1:
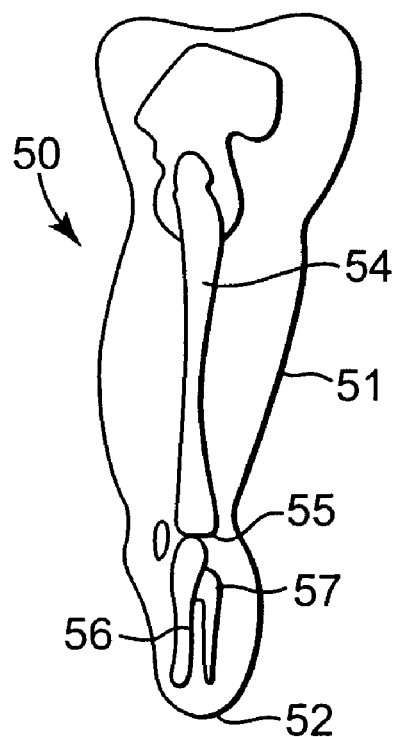
FIG. 1 shows a residual lower limb.
Figure 2:
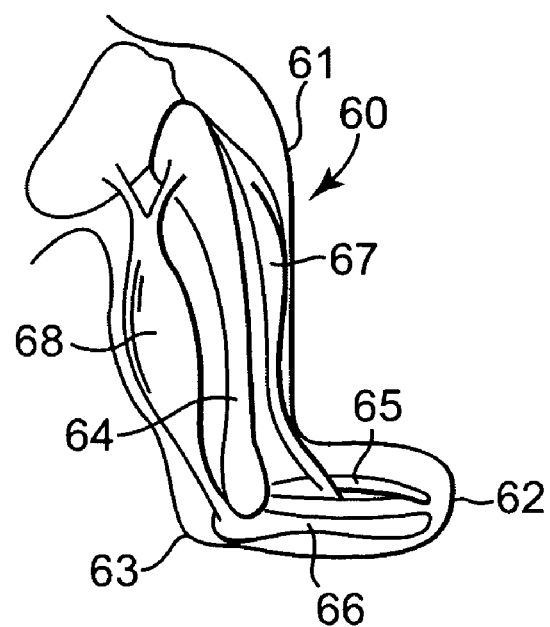
FIG. 2 shows a residual upper limb.
Figure 3:
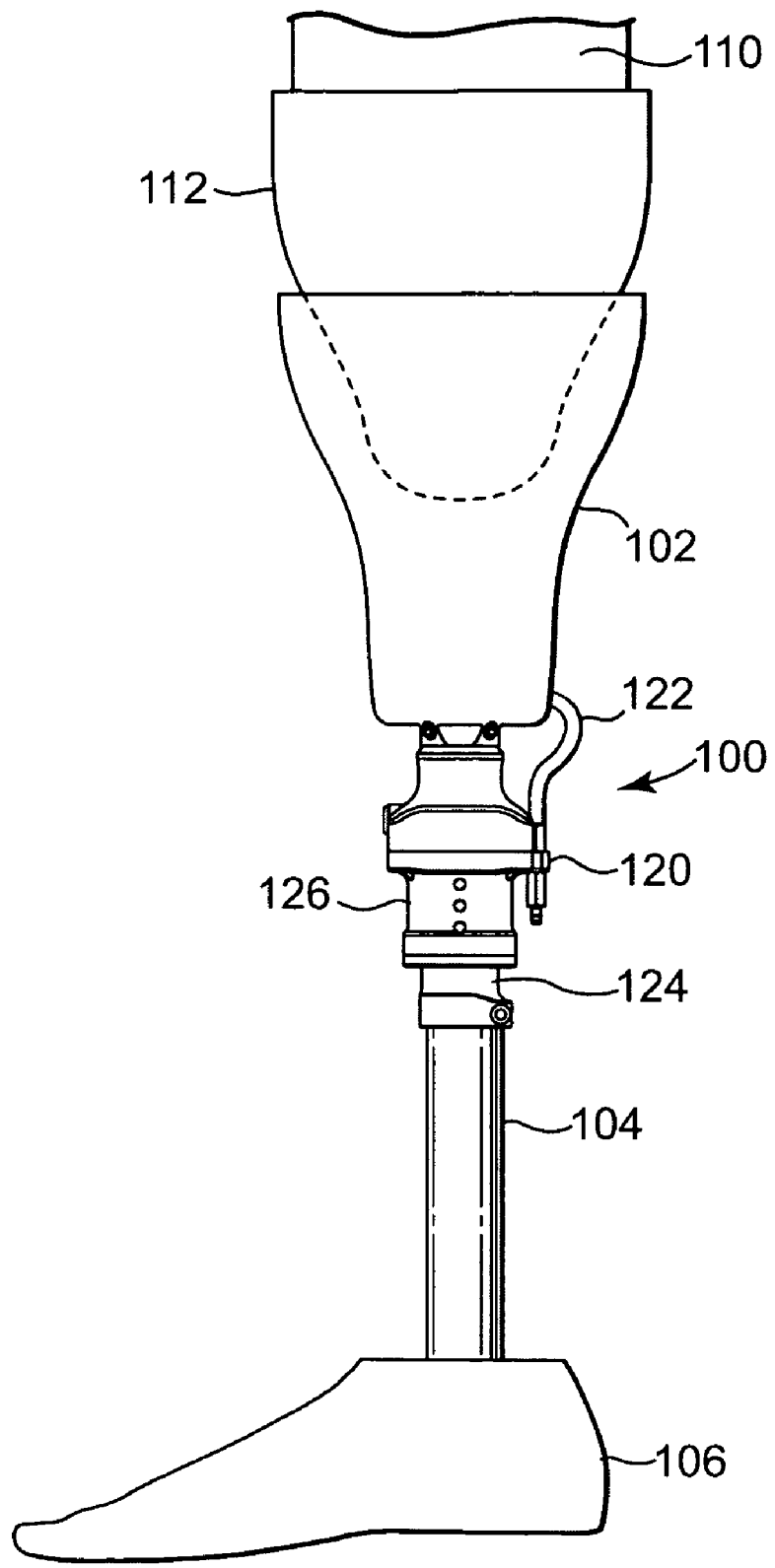
FIG. 3 shows an artificial limb engaged with a residual limb and including a socket, vacuum pump, pylon and foot.
Figure 4:
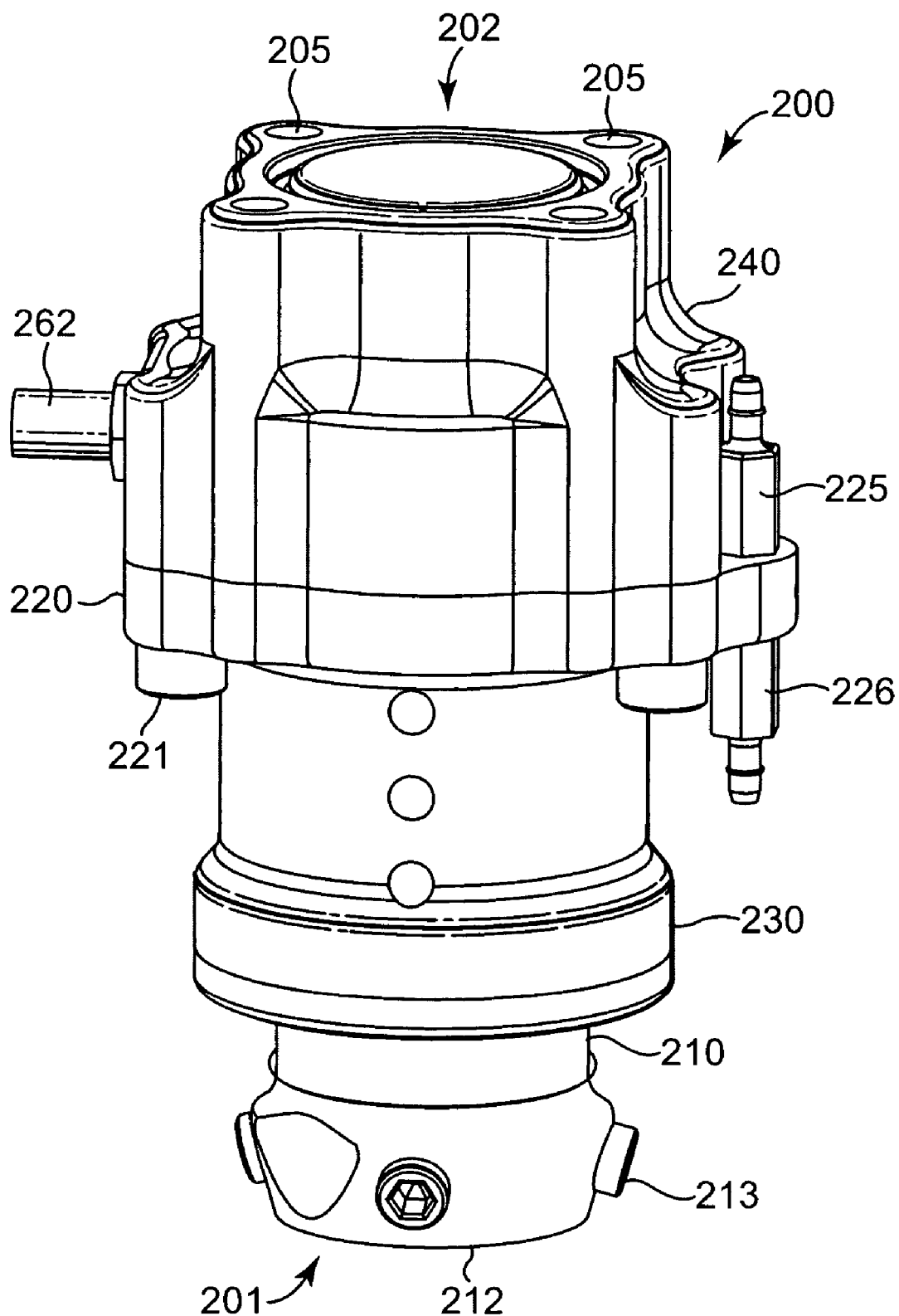
FIG. 4 shows a first embodiment of a vacuum pump in accordance with the present invention includes controlled rotation and shock absorption.
Figure 5:
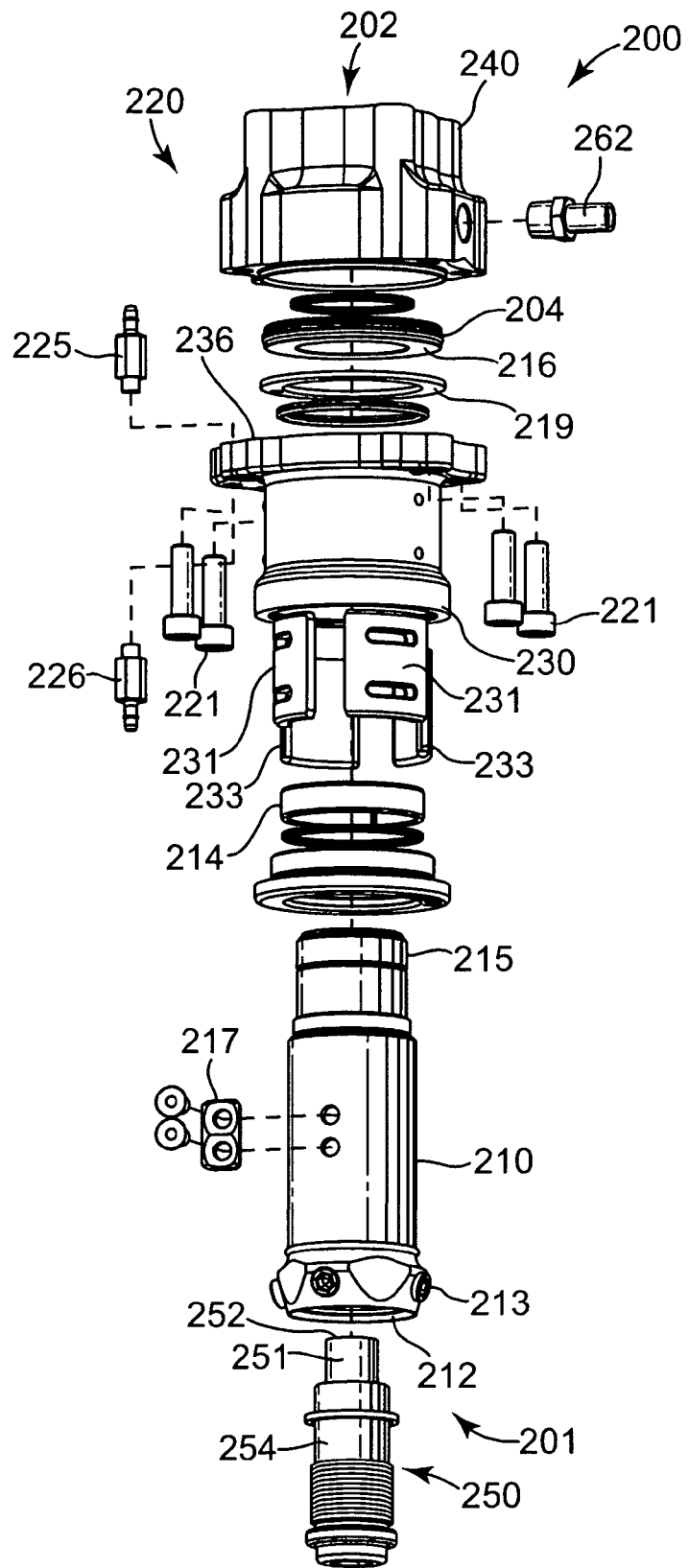
FIG. 5 is an exploded view of the pump of FIG. 4.
Figure 6:
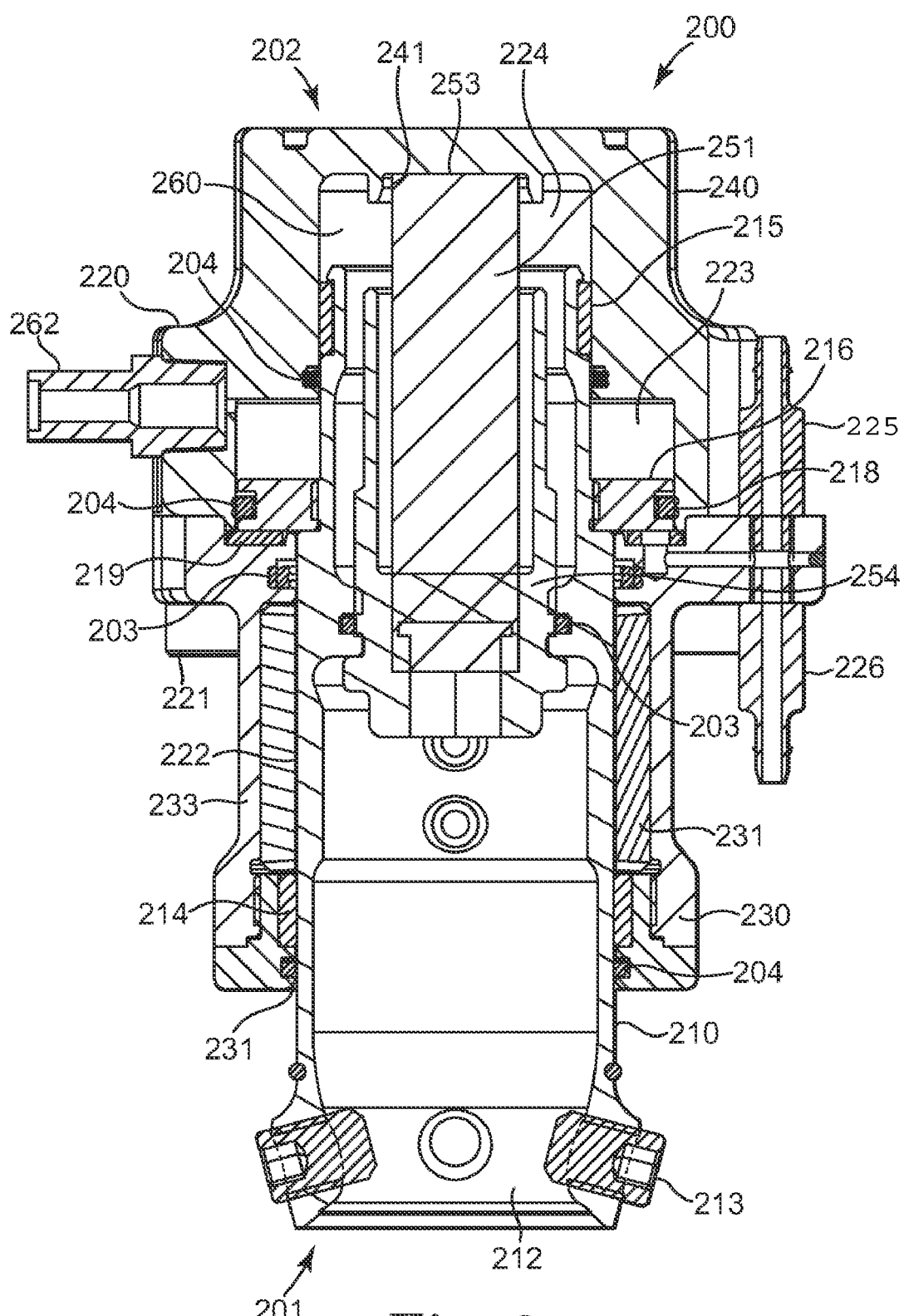
FIG. 6 is a first cross-sectional view of the pump of FIG. 4.
Figure 7:
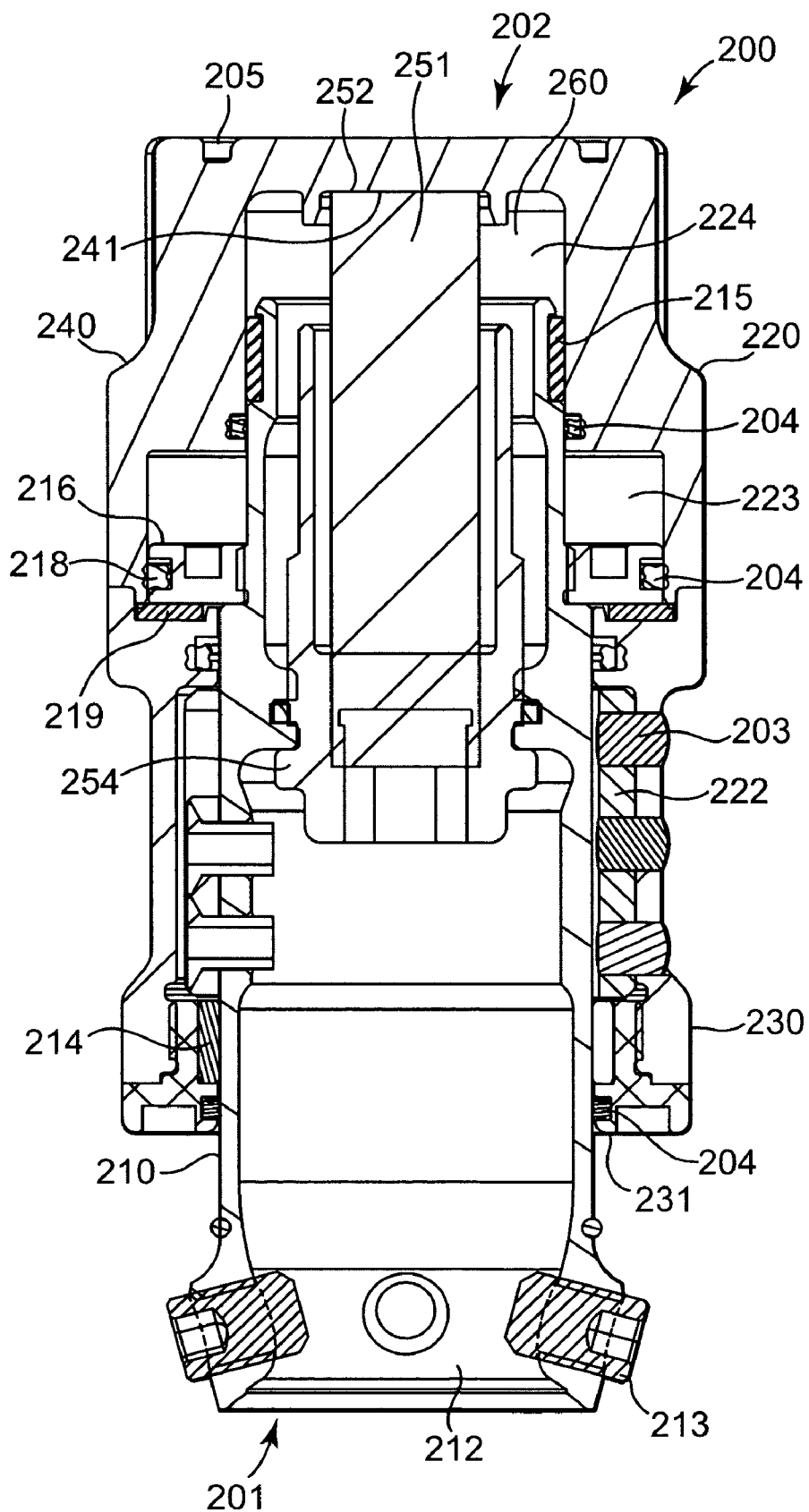
FIG. 7 is a second cross-sectional view of the pump of FIG. 4 transverse from FIG. 6.
Figure 8:
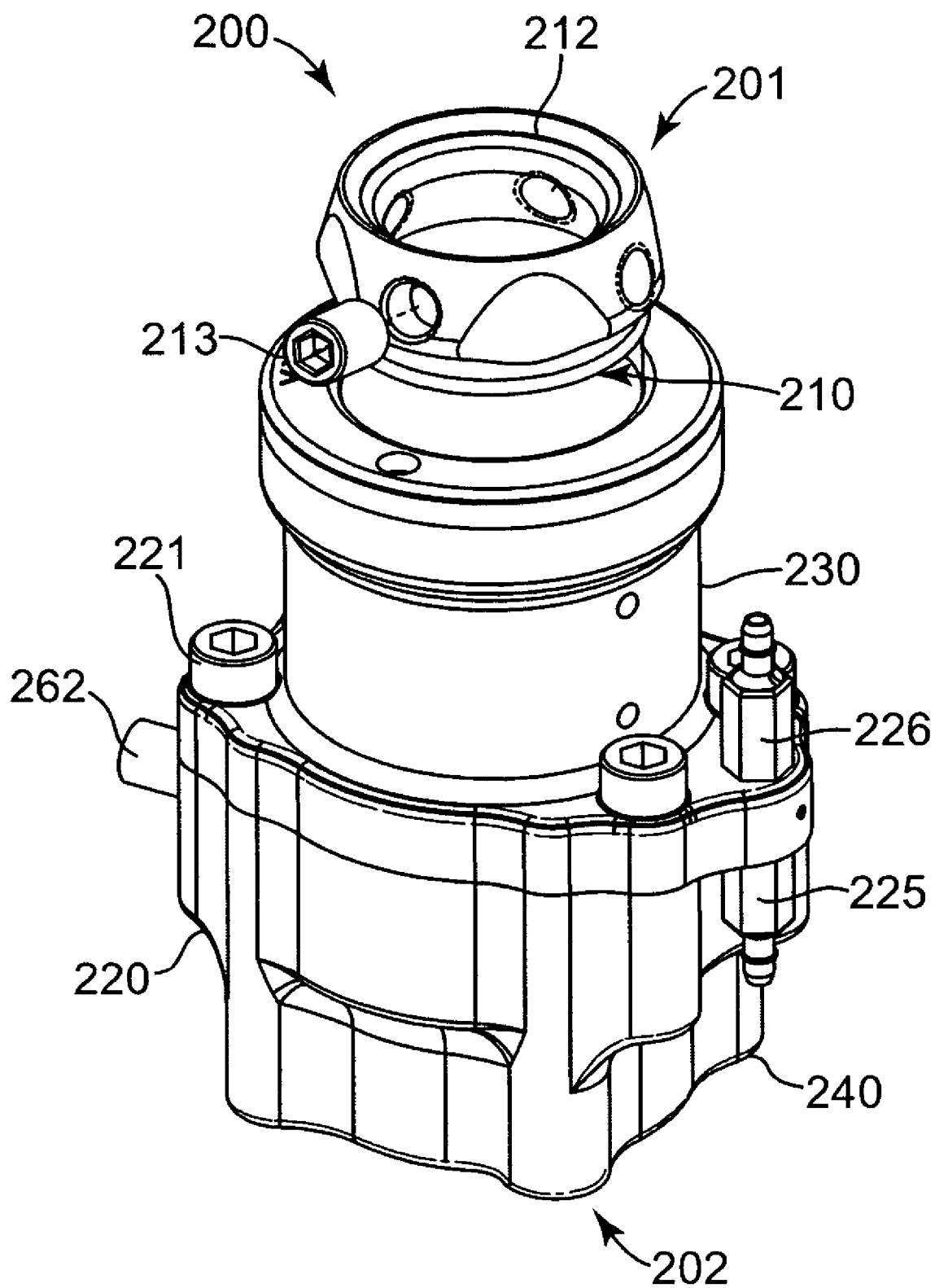
FIG. 8 is a reverse perspective view of the pump of FIG. 4.
Figure 9:
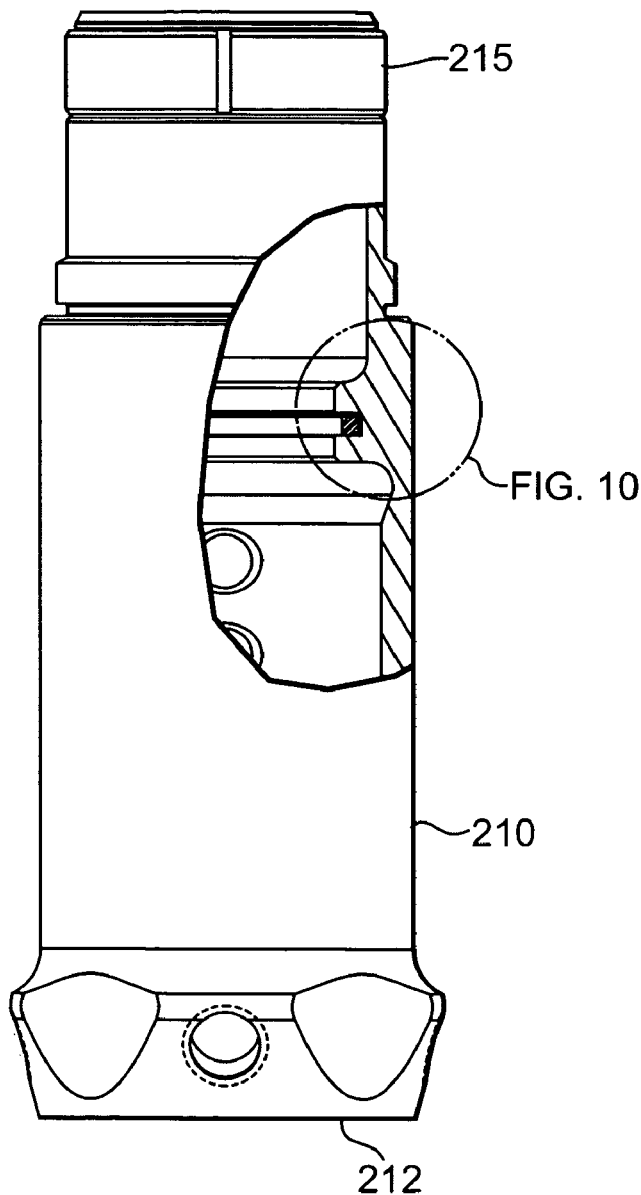
FIG. 9 is a side view and partial cross-sectional view of a shaft usable in the pump of FIG. 4.
Figure 10:
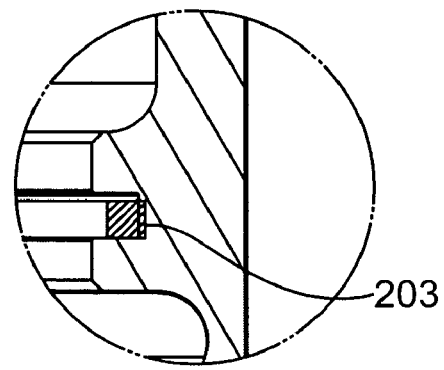
FIG. 10 is a detailed cross-sectional view of a seal inside the shaft of FIG. 9.
Figure 11:
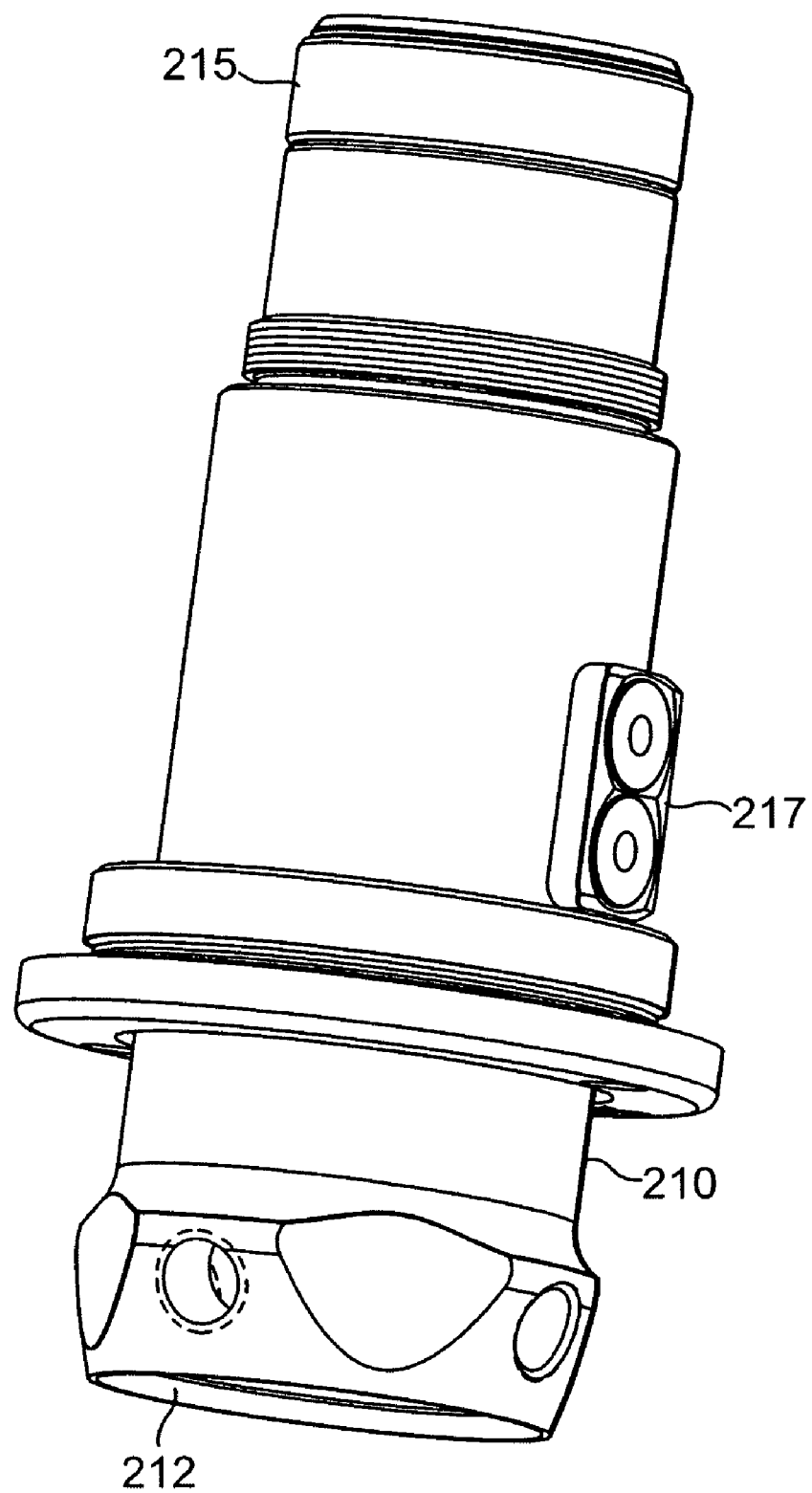
FIG. 11 is a perspective view of the shaft of FIG. 9, including a housing mounting ring.
Figure 12:
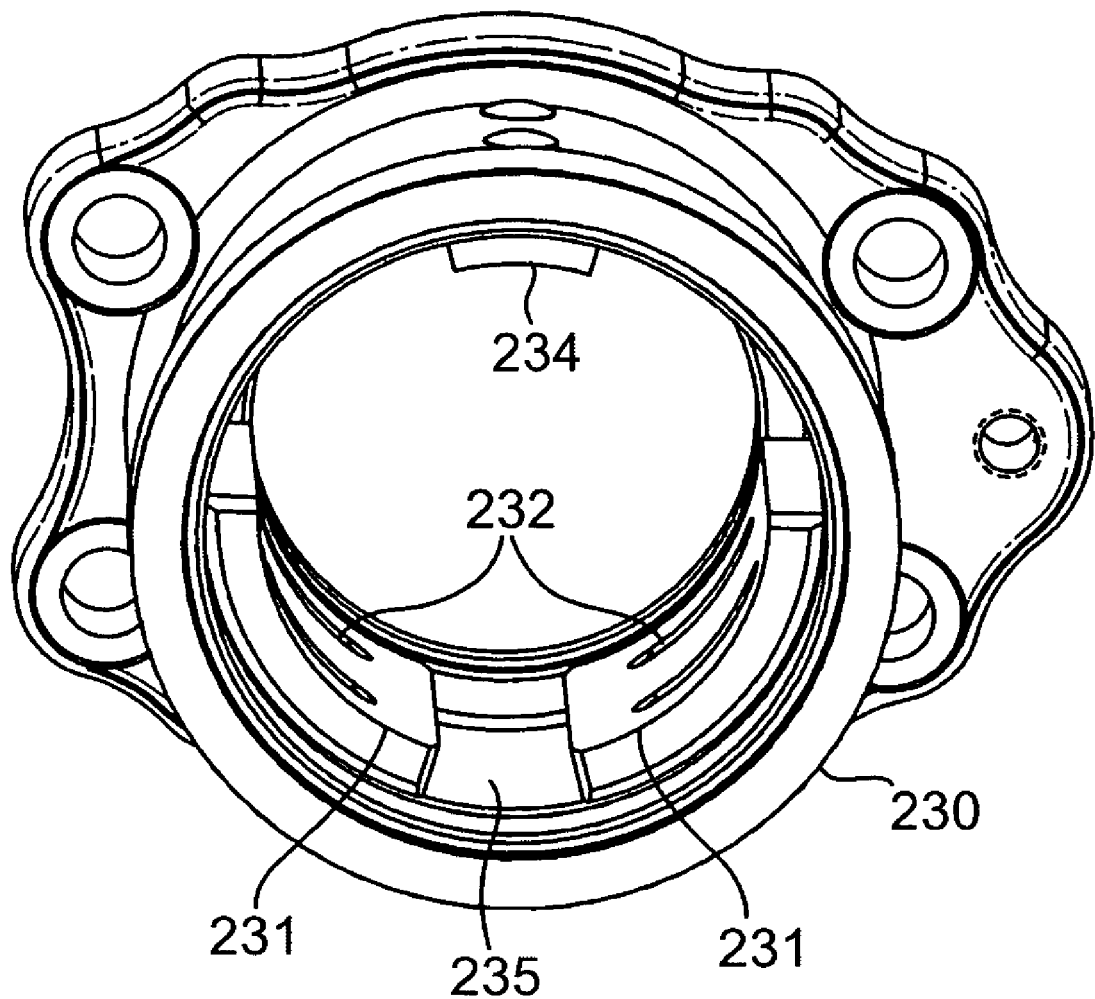
FIG. 12 is a bottom view of a housing base of the pump of FIG. 4, highlighting one half of the inner diameter components.
Figure 13:
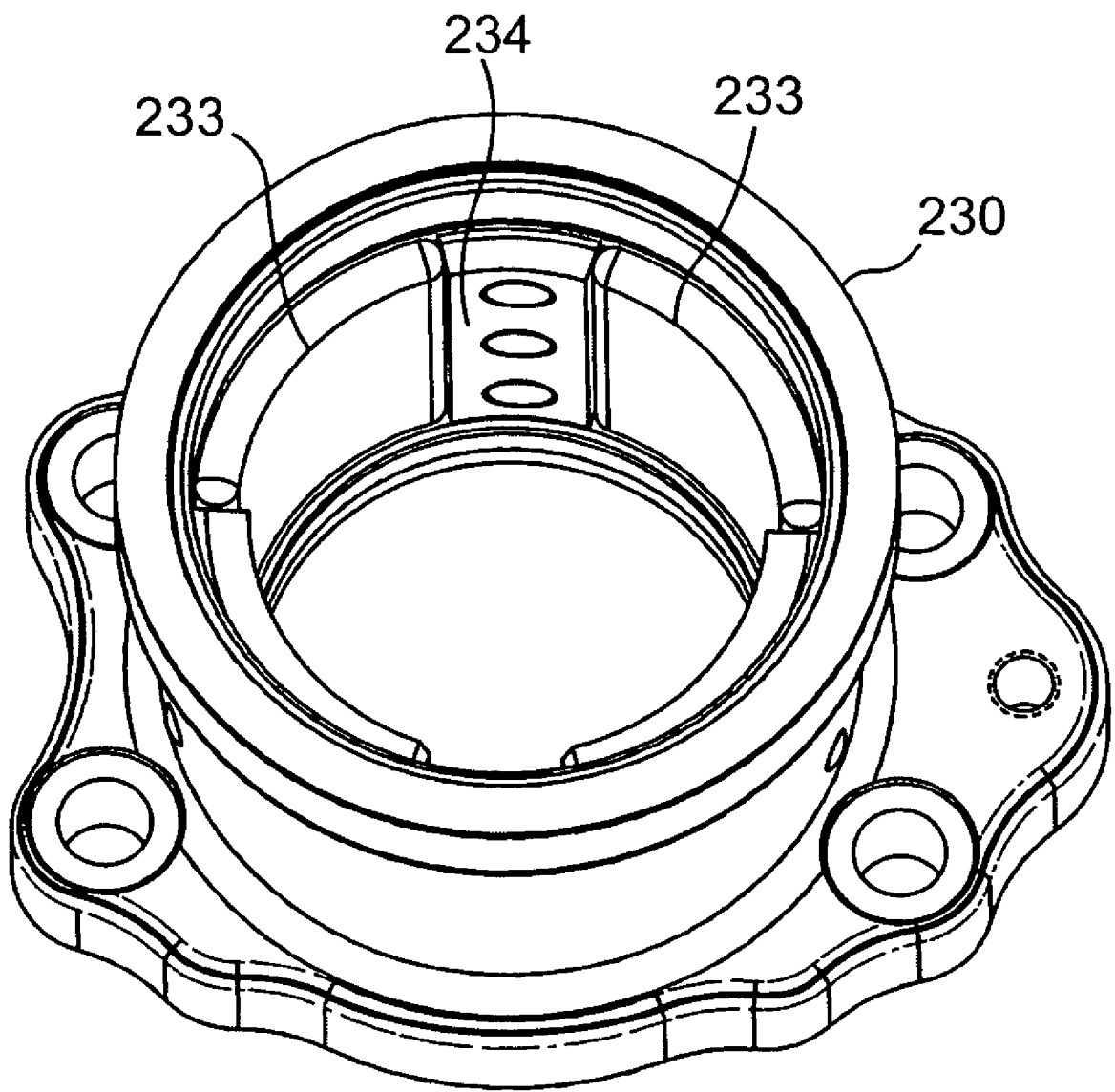
FIG. 13 is another bottom view of the housing base of FIG. 12, highlighting the other half of the inner diameter components.
Figure 14:
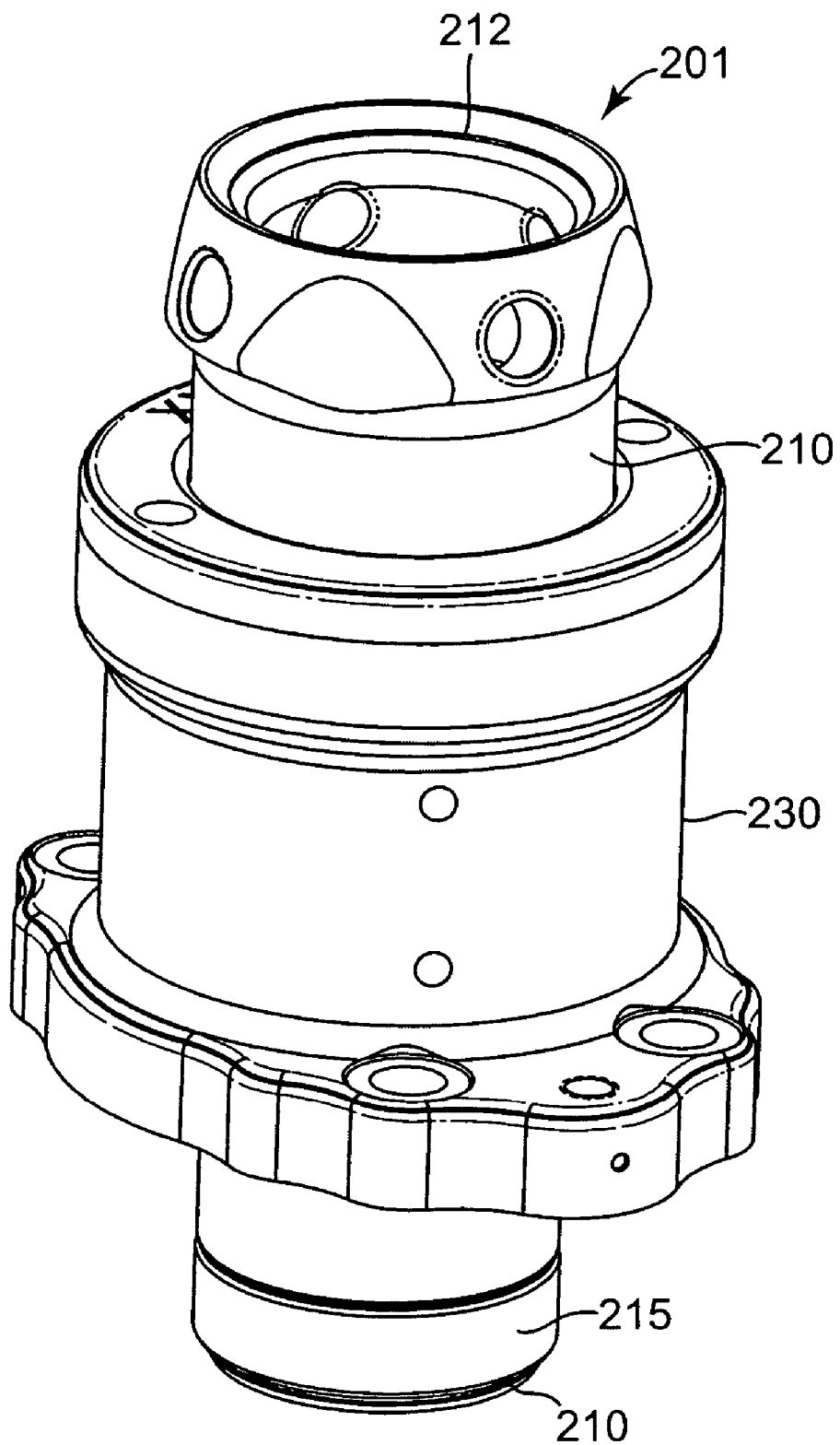
FIG. 14 is a perspective bottom view of the shaft and base housing of the pump of FIG. 4.
Figure 15:
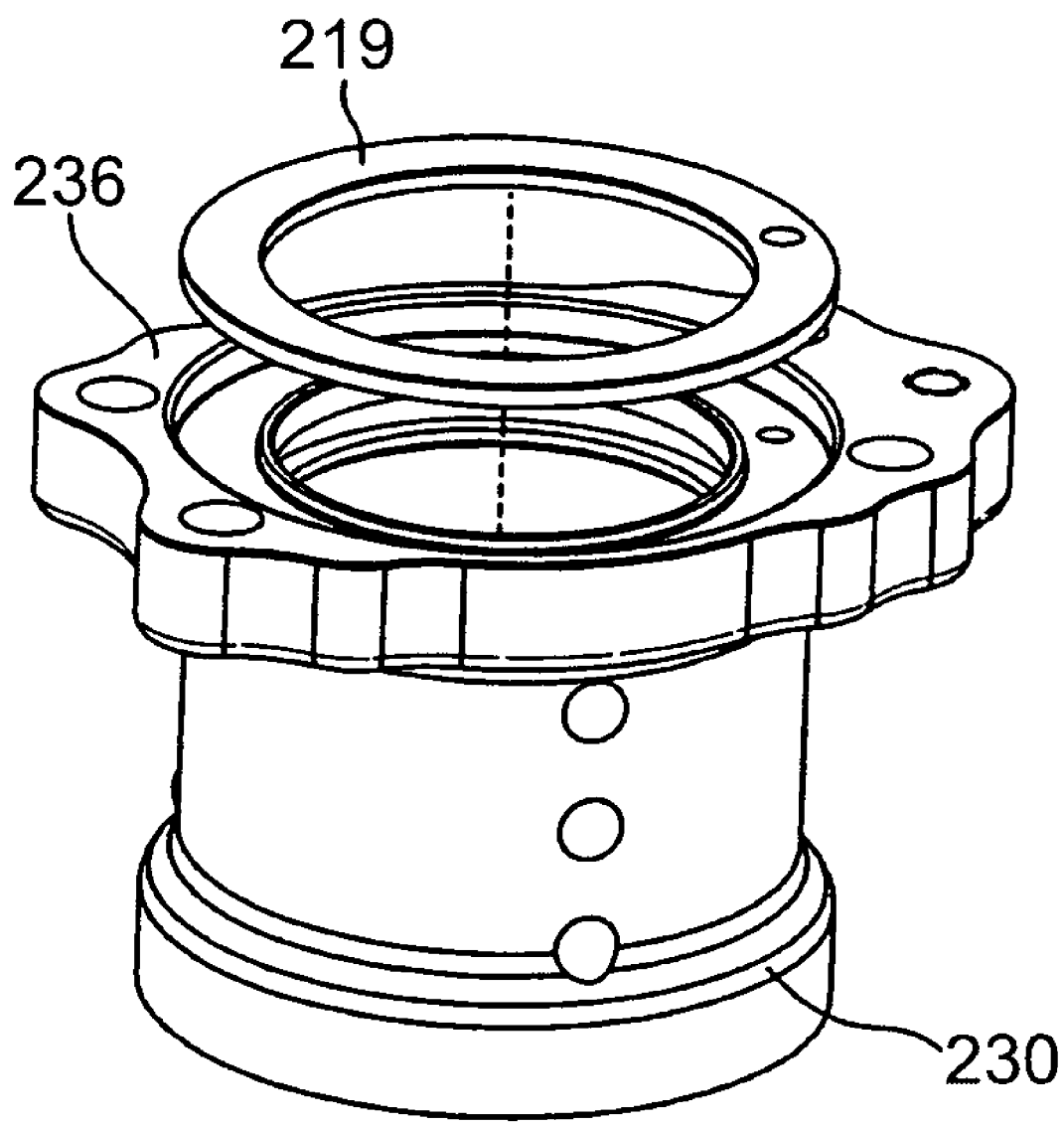
FIG. 15 is a perspective view of the top side of the base housing.
Figure 16:
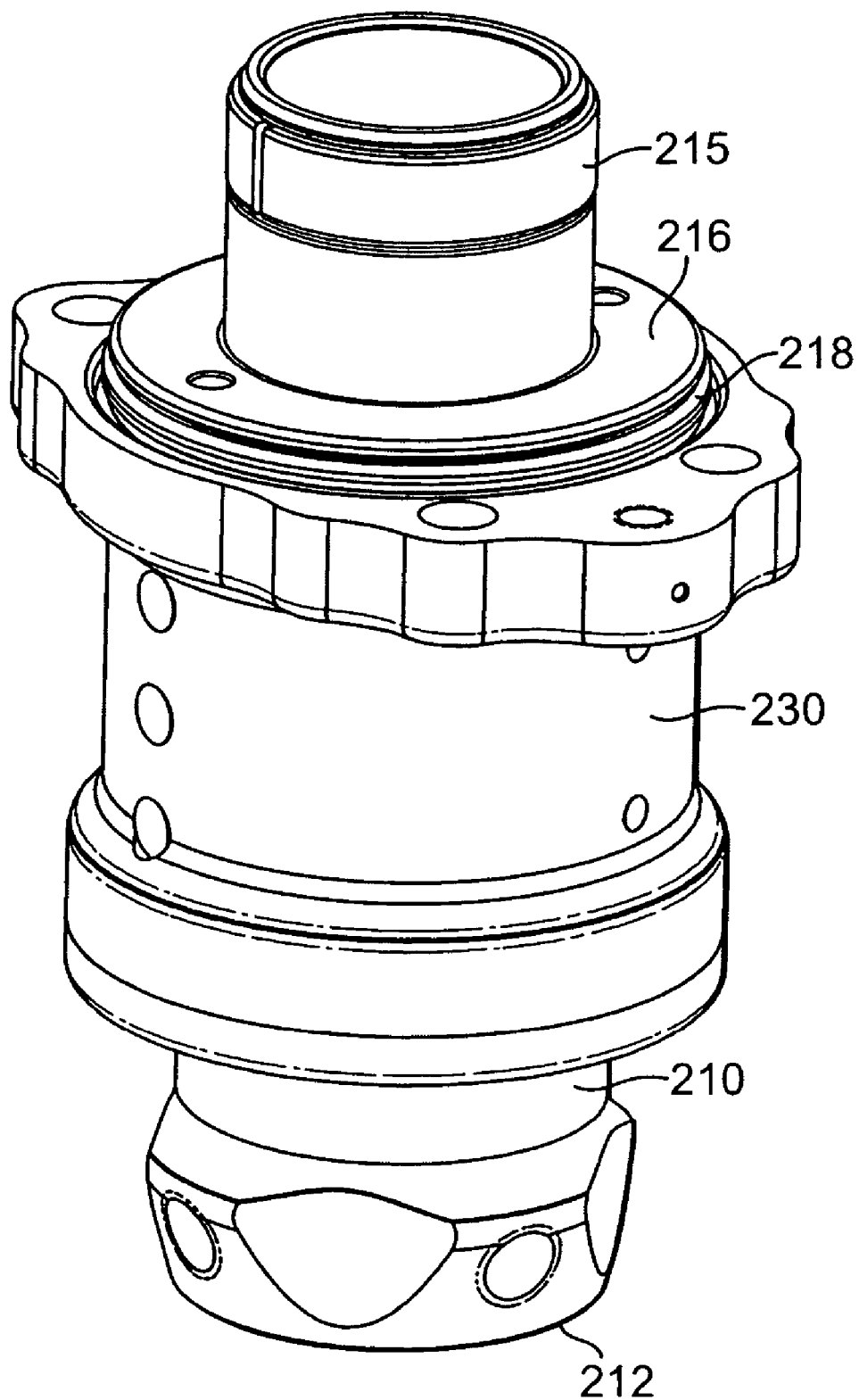
FIG. 16 is a perspective top view of the shaft and base housing showing a piston mounted on the shaft.
Figure 17:
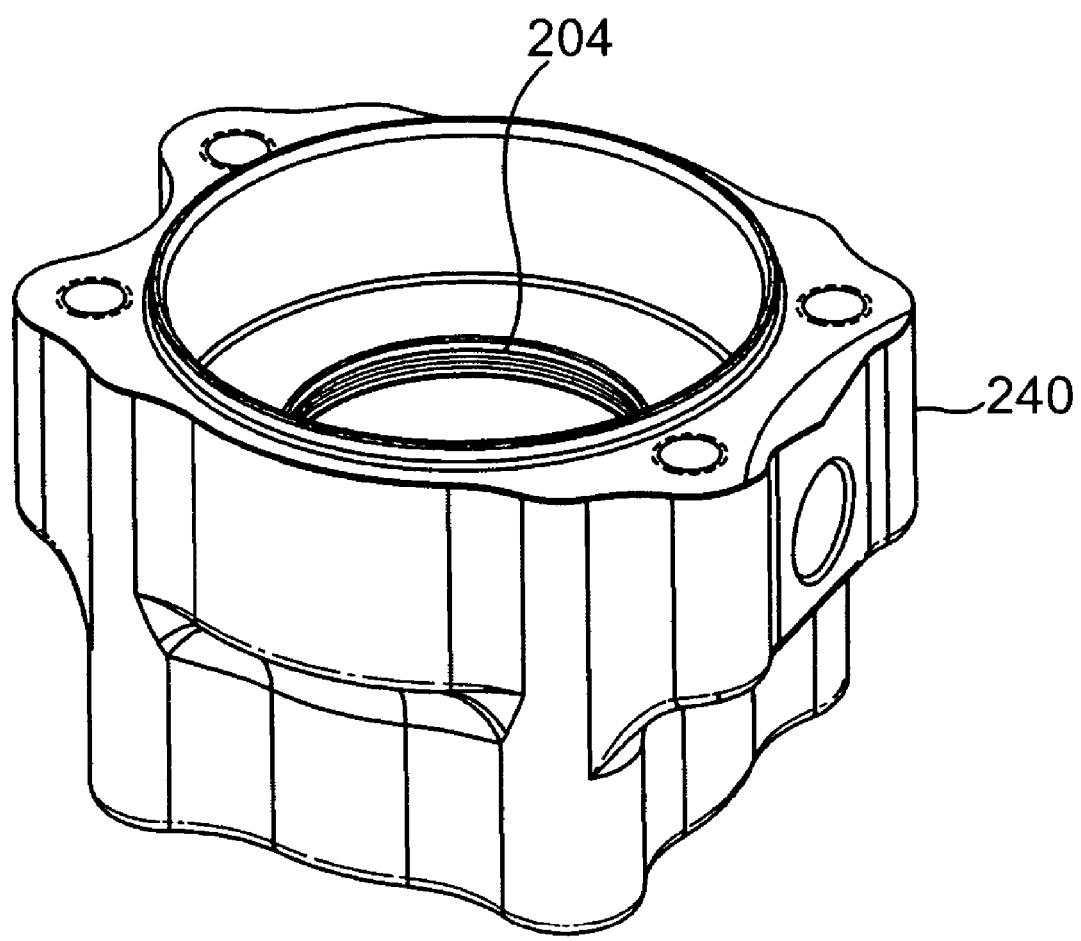
FIG. 17 is a bottom perspective view of a housing cap of the pump of FIG. 4.
Figure 18:
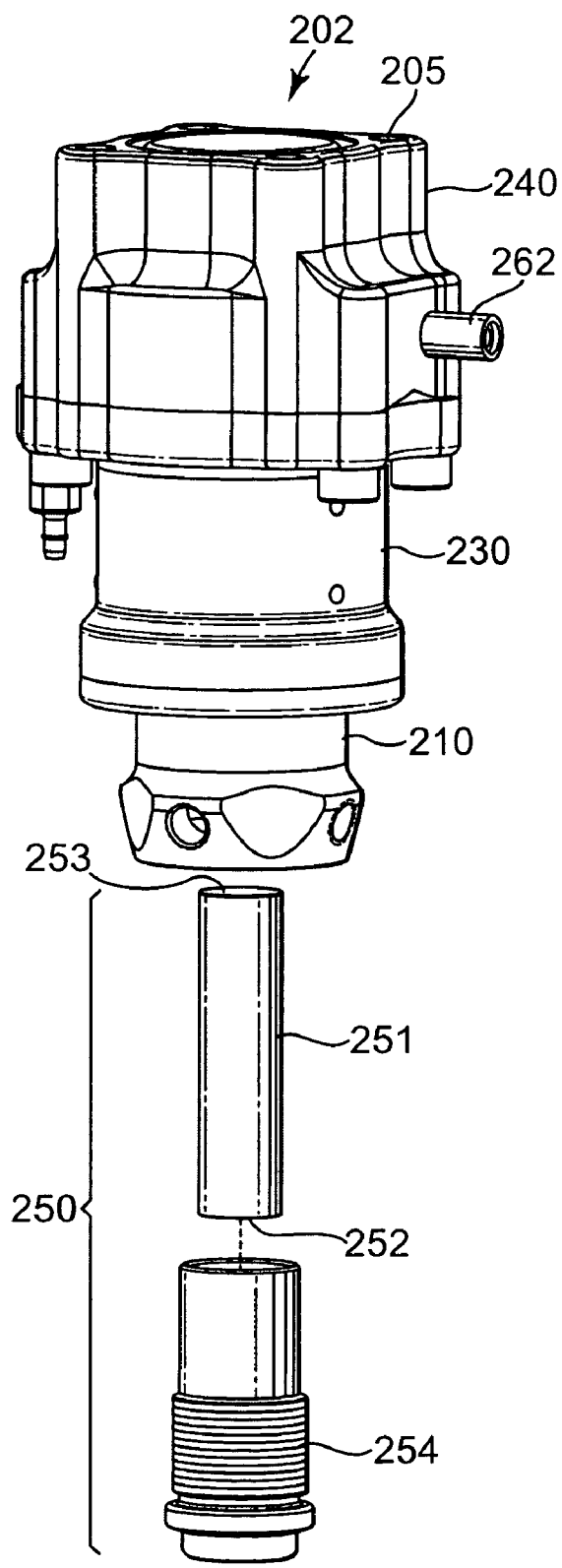
FIG. 18 is a partially exploded view of the pump of FIG. 4 showing the spring element components.
Figure 19:
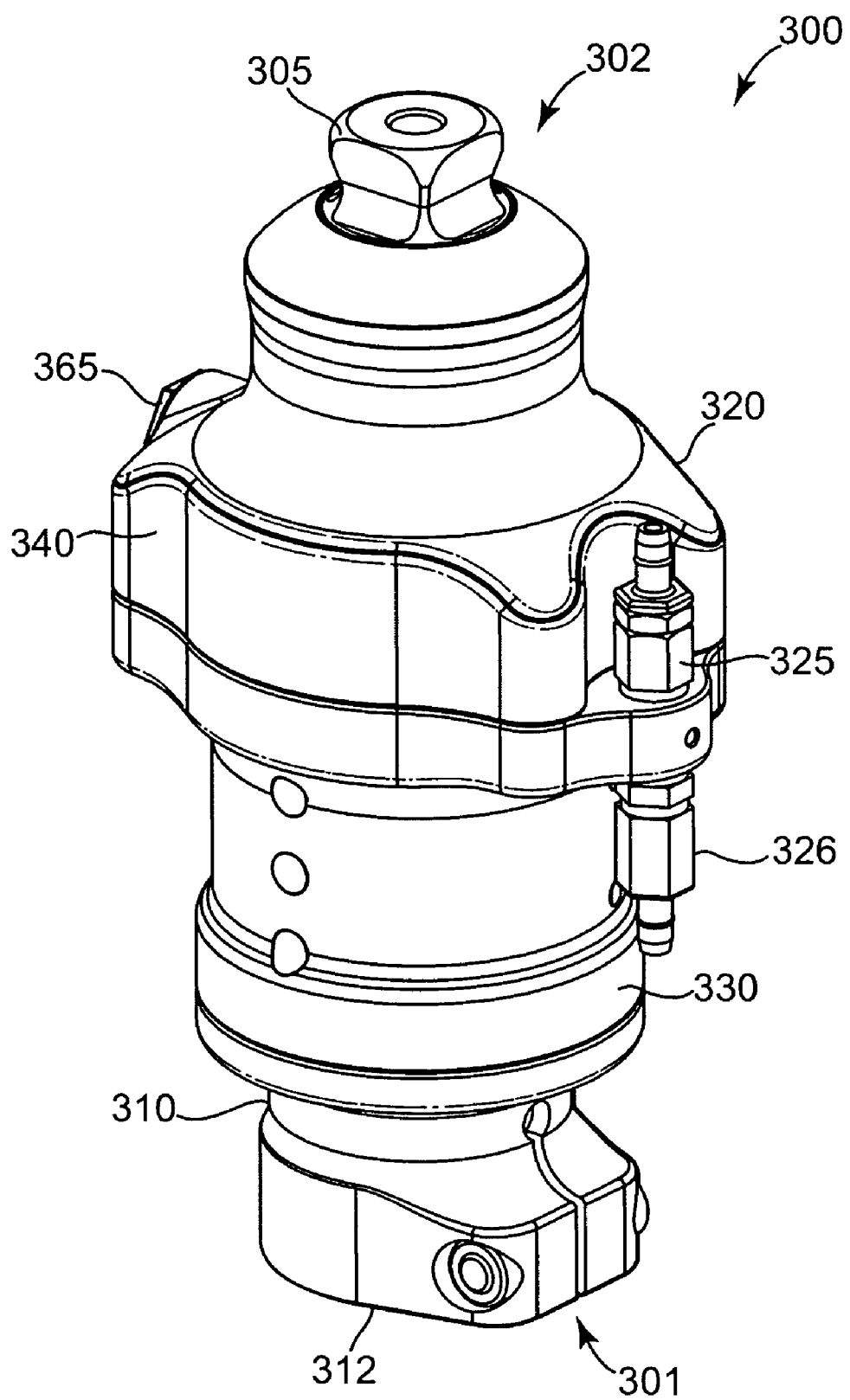
FIG. 19 is a perspective view of a second embodiment of a vacuum pump in accordance with the present invention.
Figure 20:
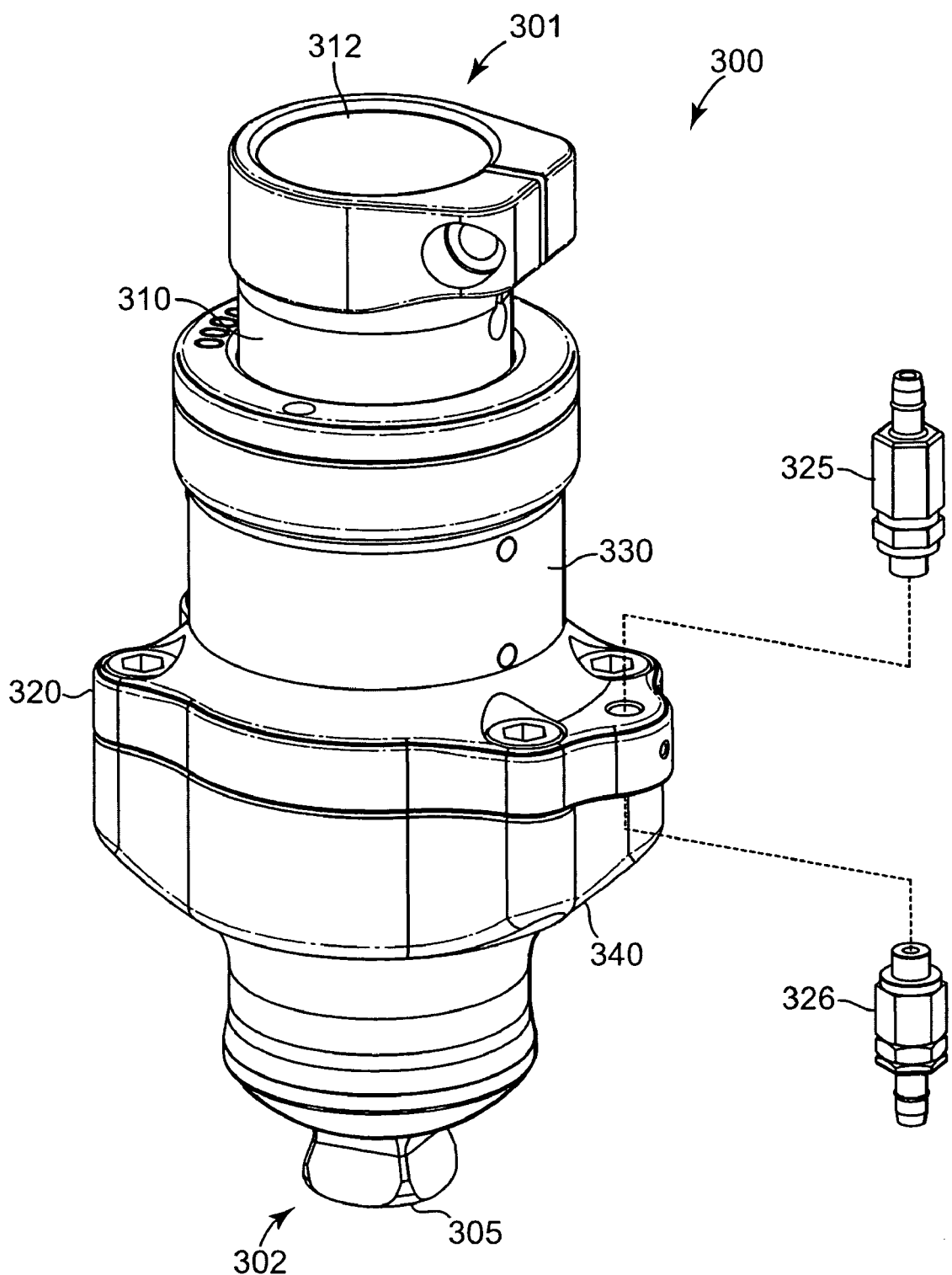
FIG. 20 is a bottom perspective view of the pump of FIG. 19.
Figure 21:
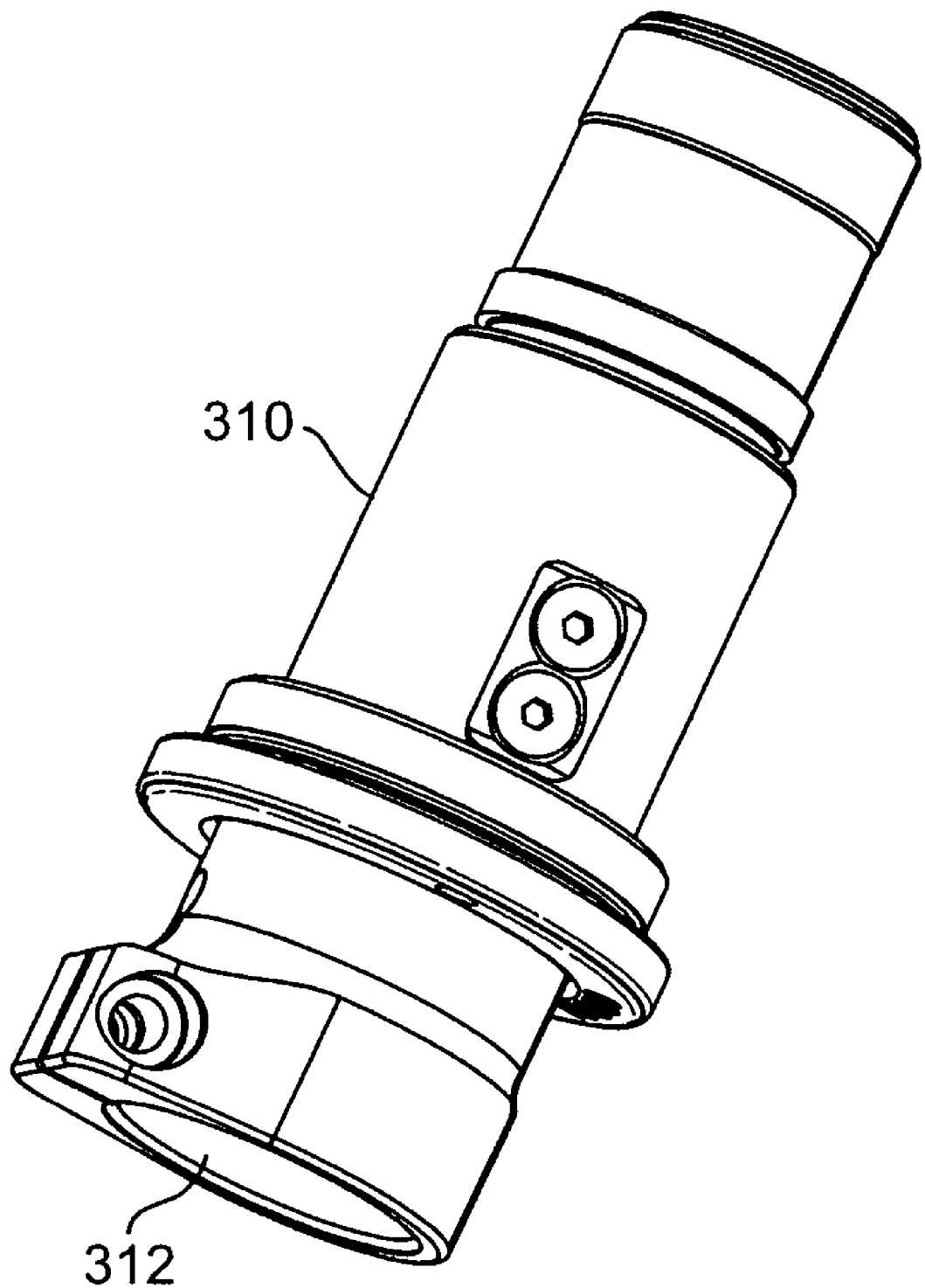
FIG. 21 is a perspective view of a shaft usable with the pump of FIG. 19.
Figure 22:
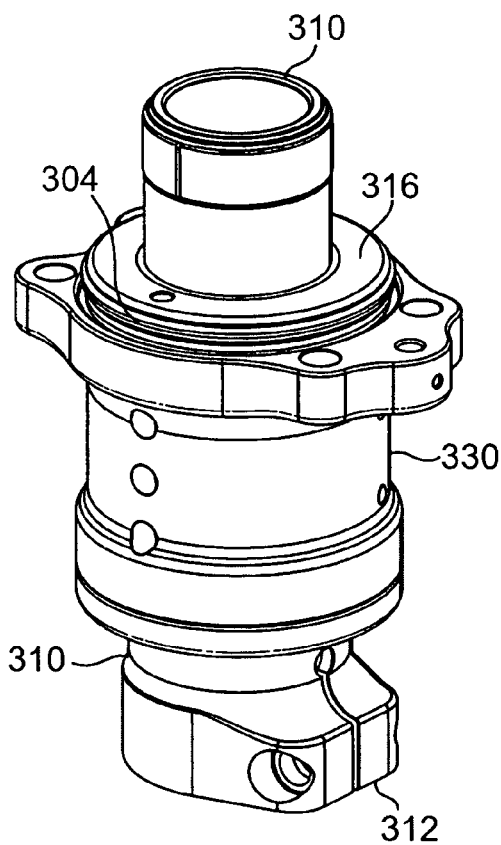
FIG. 22 is a perspective view of the shaft and base housing of the pump of FIG. 19, showing a piston.
Figure 23:
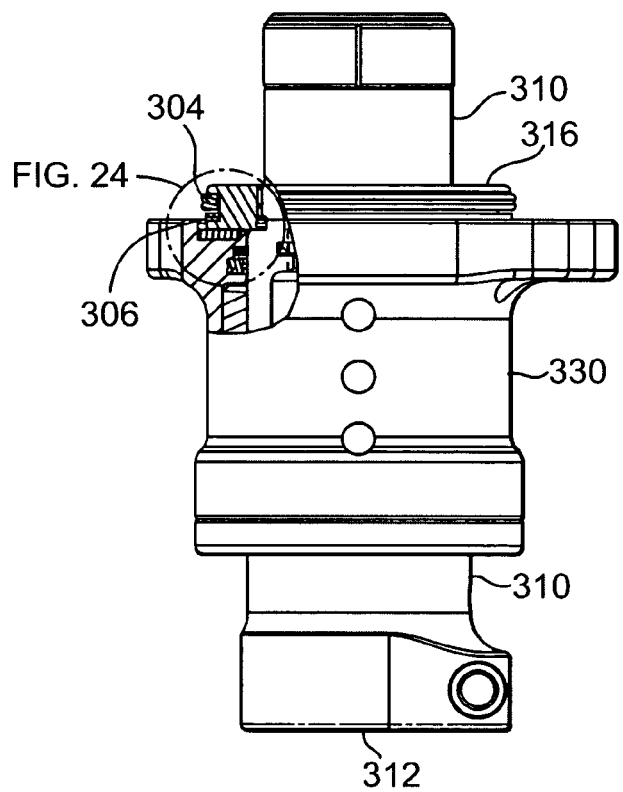
FIG. 23 is a partial cross-sectional side view of the components of FIG. 22, highlighting the seals provided within the housing.
Figure 24:
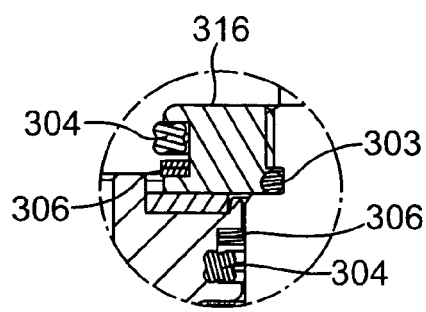
FIG. 24 is a detailed view of the seals of FIG. 23.
Figure 25:
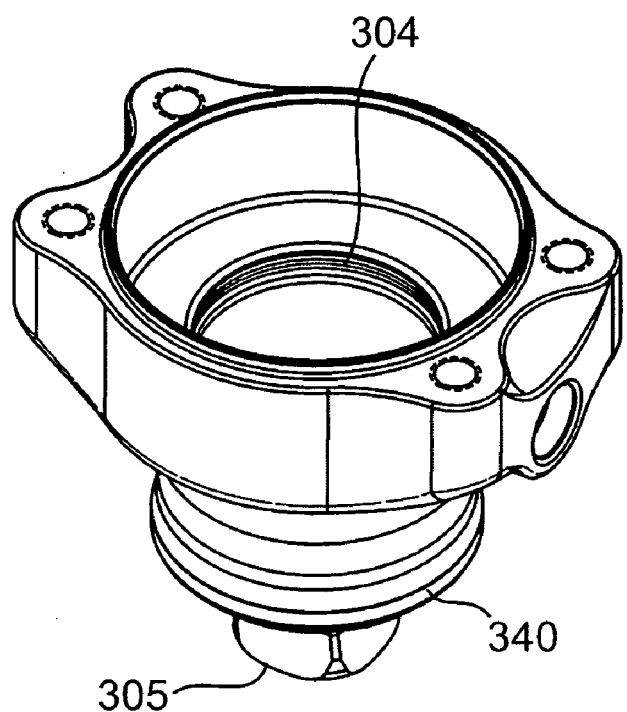
FIG. 25 is a bottom perspective view of a housing cap of the pump in FIG. 19.
Figure 26:
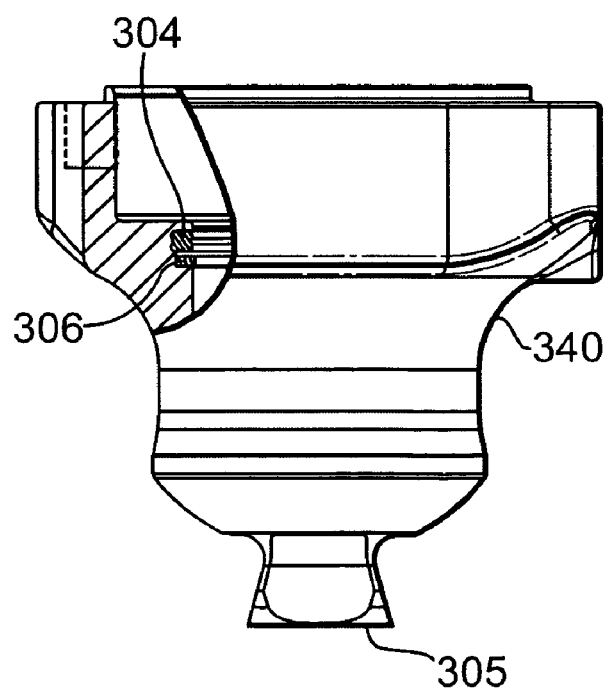
FIG. 26 is a side view of the cap of FIG. 26.
Figure 27:
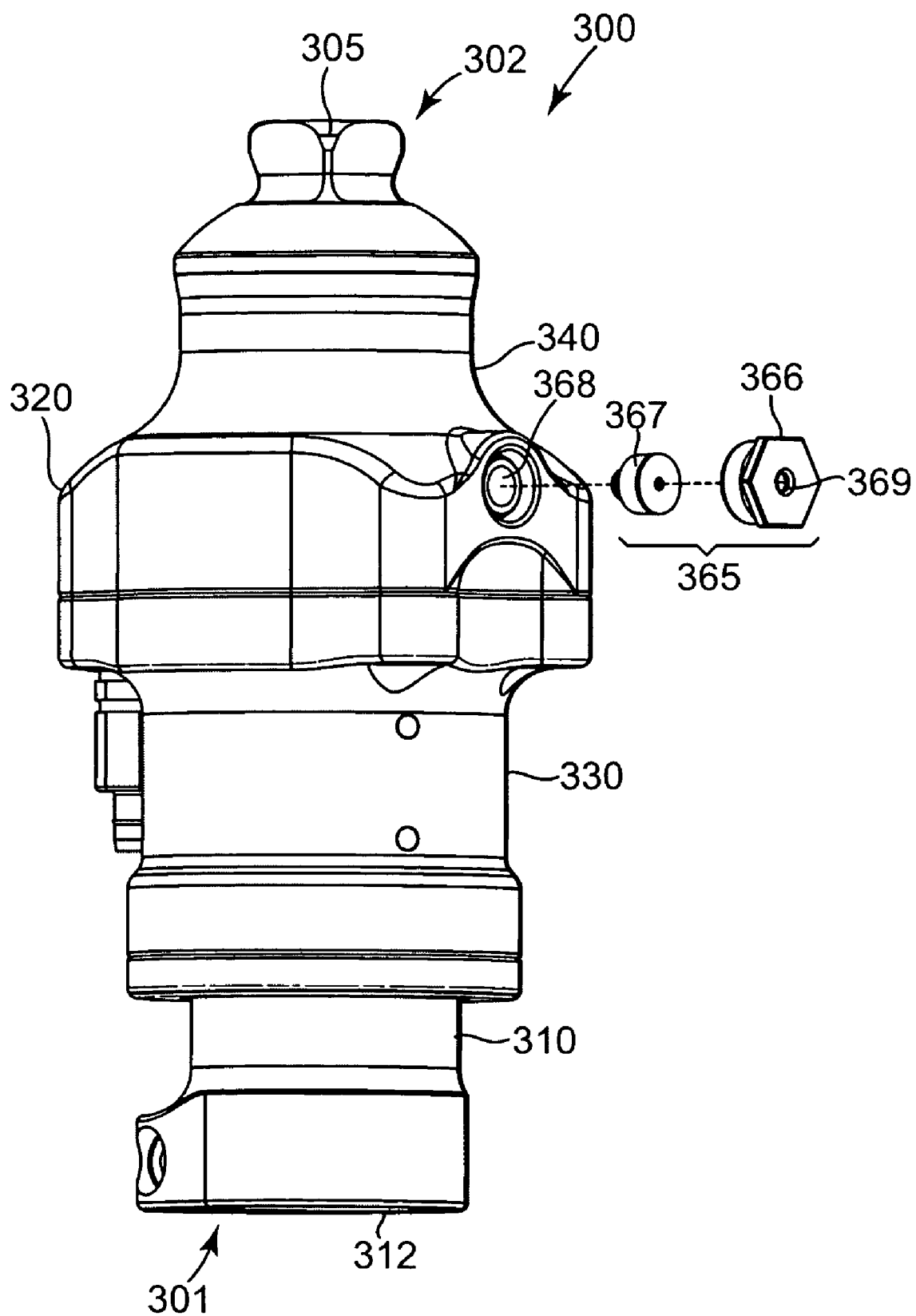
FIG. 27 is a partially exploded view of the pump of FIG. 19, showing the air valve connected to the pneumatic spring.
Figure 28:
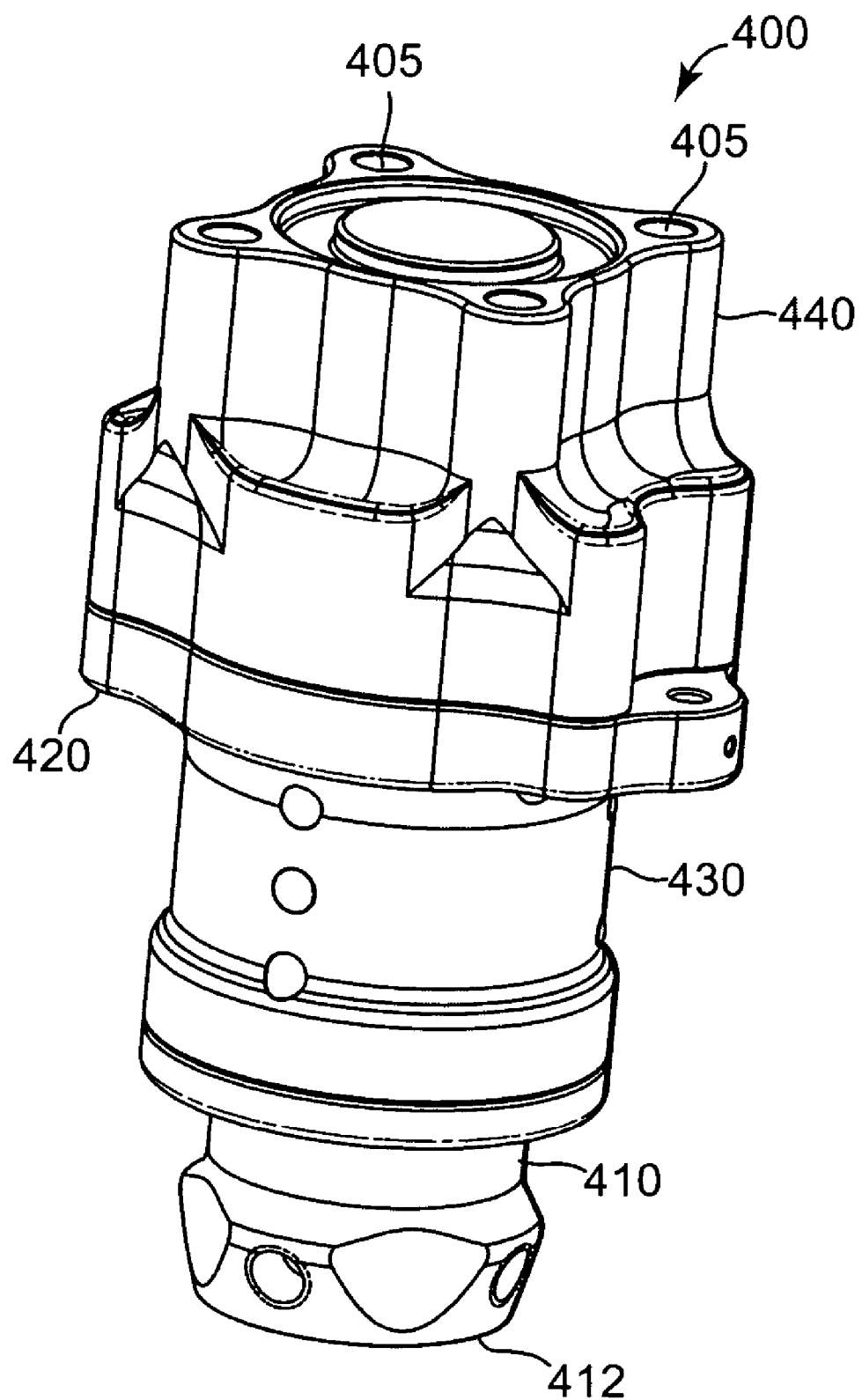
FIG. 28 shows a third embodiment of a vacuum pump in accordance with the present invention.
Figure 29:
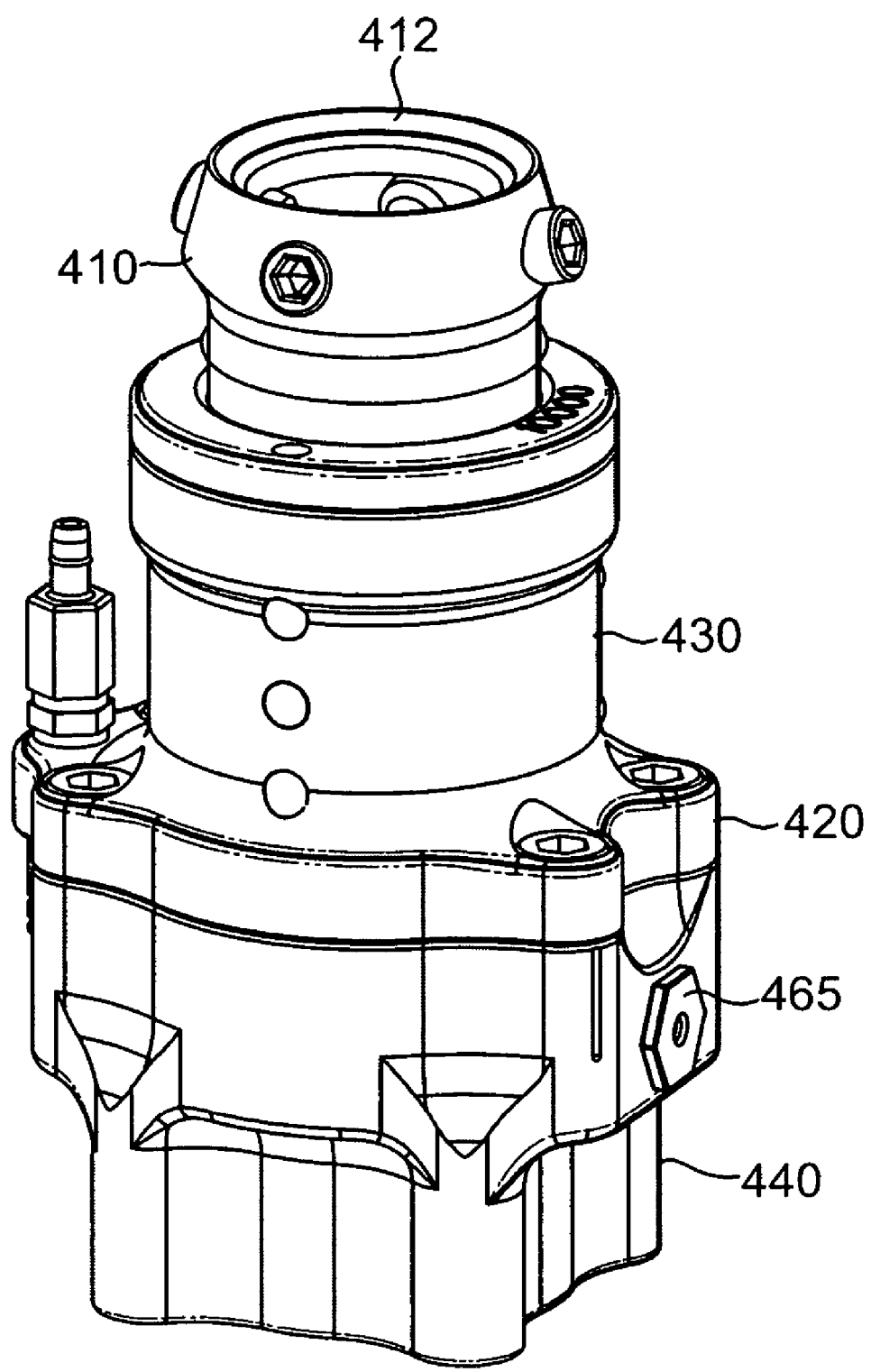
FIG. 29 is a bottom perspective view of the pump of FIG. 28.
Figure 30:
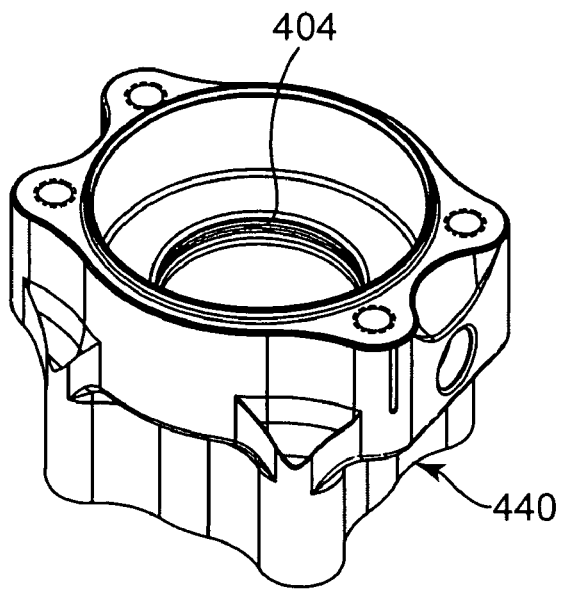
FIG. 30 is a bottom perspective view of a housing cap of the pump of FIG. 28.
Figure 31:
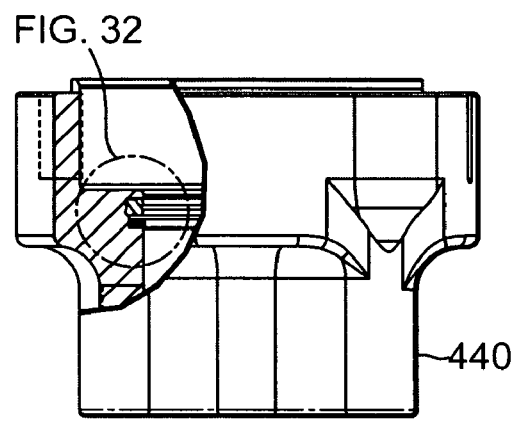
FIG. 31 is a partial cross-sectional side view of the cap of FIG. 30, highlighting the seals provided within the housing.
Figure 32:
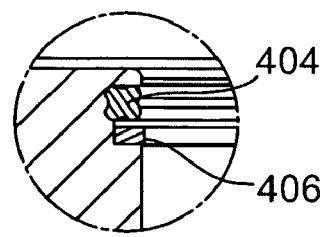
FIG. 32 is a detailed view of the seals of FIG. 31.

One embodiment of the present invention provides a vacuum pump and compressive shock absorber with controlled rotation for use with an artificial limb, such as an artificial leg, artificial arm or other prosthetic device. As shown in FIG. 3, in one example, an artificial leg 100 includes a socket 102 coupled to one end of a pylon 104 via a vacuum pump 120 in accordance with the present invention. An artificial foot 106 is coupled to the other end of the pylon 104. A residual limb, or residuum 110, of a user is encased in a liner 112 and is received within the socket 102 that has been configured in size and shape to accept the residuum 110. A fluid connection, such as tube 122, connects the vacuum pump 120 to the socket 102.

As described above, the vacuum pump 120 removes gas from the space between the prosthetic liner 112 and the socket 102 after placement of the residuum 110 and liner 112 within the socket 102. The socket 102 can also be arranged so that gas is removed from between the liner 112 and skin of the residuum 110, which would facilitate removal of perspiration. Besides aiding in the retention of the artificial leg 100 on the residuum 110, removal of the gas from between the socket 102 and liner 112 increases the intimacy of the socket fit, improving the user's ability to feel shock waves passed through the prosthetic structure, or artificial leg 100, and into the residuum 110. This can result in a "feeling" sensation and in increased awareness as to the location of the artificial leg 100 under the user. As used hereinafter, air may mean any appropriate type of gas, including oxygen, nitrogen or air.

In one embodiment, the vacuum pump 120 is configured for an in-line mounting between the socket 102 and pylon 104. As described in more detail below, the vacuum pump 120 includes a shaft 124 that reciprocates within a pump housing 126 during motion of the artificial leg 100. As the user takes a step and places force and/or weight on the leg 100, the shaft 124 moves into the housing 126. When the user moves through the swing phase with the artificial leg 100, and removes force and/or weight from the leg 100, the shaft 124 extends or moves out from the housing 126. This reciprocal motion drives the pump 120 to pull the air out of the socket 102 via tube 122.

As shown in FIGS. 4-18, a first embodiment of a vacuum pump 200, in accordance with the present invention, is shown including a shaft 210 and a housing 220. At a first end 201 of the pump 200, the shaft 210 includes an integral coupler 212 formed as a receiver to receive a prosthetic structure, such as prosthetic pyramid, pylon 104 or other suitable structure. A plurality of fasteners, such as four set screws 213, are provided to secure or fasten the prosthetic structure to the shaft 210 at the coupler 212. Providing an integral coupler 212 can be more cost effective and robust than other models using a separate coupler, although a separate coupler would work. At an opposite end 202 of the pump 200, the housing 220 is configured to receive a suitable connector, such as a pyramid connector commonly used in the prosthetic industry or any other suitable connector. The housing 220 is provided with a four-hole bolt pattern 205 common to prosthetic components, allowing the attachment of variety of different types of components.

The housing 220 includes a base 230 and a cap 240 both configured to mate with each other and be secured together. In this embodiment, the base 230 and cap 240 are bolted together with bolts 221, however, other types of securement or fastening methods, means and mechanisms are also possible. The housing 220 includes a chamber 222 into which the shaft 210 is inserted through an opening 231 in the base 230 and within which the shaft 210 reciprocates. The housing 220 and shaft 210 together form a pump or vacuum chamber 223 and a shock absorption chamber 224.

A first bearing or bushing 214 is provided in the base 230 and a second bearing or bushing 215 is provided in the cap 240, on opposite sides of the vacuum chamber 223, to support the shaft 210 during reciprocation. In this embodiment, the first bearing 214 is positioned and secured into an inner diameter of chamber 222 in the base 230. The second bearing 215 is positioned around and secured to an end of the shaft 210 which rides within the cap 240. It is to be understood, however, that other positions and methods or means of securement or fastening of the bearings, as well as the use of additional bearings, are also possible and within the scope of the present invention. The present bearing configuration provides a wider spacing between the bearings 214, 215 than previous similar pumps. Such wider spacing allows for higher loads from heavier users and/or more strenuous activities, or, conversely, reduces the stresses in the structural components and the load on the bearings, which reduces bearing wear. In one embodiment, the bearings 214, 215 are formed with a steel backing covered with a layer of sintered bronze and a final layer of PTFE or Teflon®. Suitable bearings are available from PEER, Inc. of Waukegan, Ill.

Numerous seals, such as O-rings 203 and X-rings 204, are also provided along the chamber 222 to seal the various chambers with respect to the shaft 210. The X-ring seals 204 provide greater cross-section for enhanced sealing of the chambers of the pump 200.

A piston 216 is coupled to the shaft 210 and positioned within the vacuum chamber 223. In this embodiment, the piston 216 screws onto threads provided on the shaft 210, however, other methods or means of securement or fastening are also possible. Reciprocation of the shaft 210 results in reciprocation of the piston 216 within the vacuum chamber 223. A piston seal 218 is provided to seal the chamber with respect to the piston 216. In addition, a bumper 219 is provided within the base 230 at the cap-interface side 236. The bumper 219 is a ring of resilient material positioned adjacent the piston 216 to handle impact of the piston 216 at a base end of the stroke.

An intake valve 225 is mounted to the housing 220 and is provided in fluid communication with the vacuum chamber 223. In one embodiment, the intake valve 225 is a rubber, duckbill style check valve, including an integral filter. However, other types and styles of valves are also possible and within the scope of the present invention, including but not limited to ball, flapper or umbrella valves. This intake valve 225 is configured for fluid connection to a socket of the artificial limb, such as socket 102. An exhaust valve 226 is also provided in fluid communication with the vacuum chamber 223. The exhaust valve 226 may be the same type of valve as the intake valve 225, or they may be of different types and styles. Upon upward/inward stroke of the piston 216 within the vacuum chamber 223, air in the vacuum chamber 223 is expelled through the exhaust valve 226. Upon downward/outward stroke of the piston 216, air from a connected socket, such as socket 102, is pulled into the vacuum chamber 223 through the intake valve 225 and out of the socket, thereby forming a vacuum in the socket, that is, a reduced pressure environment.

The housing 220 and shaft 210 may be formed from a number of different materials. For a heavier duty vacuum pump, stainless steel is a strong and suitable material. For lighter duty pump configurations, aluminum is a suitable material. However, other materials may also be used. When aluminum is used, a coating or finish may be necessary to improve resistance to wear and corrosion, especially due to contact with perspiration. One suitable finish is an anodic process similar to hard anodizing known as Magnaplate HCR, which is provided by General Magnaplate of Ventura, Calif. However, other types of materials, coatings and finishes may also be suitable.

In the past, separate shock absorbers, pumps and rotational components would have to be coupled together between the socket and an appendage, such as a foot, in order to provide the functionality desired by the user. The multiple components required increased length in the structure, precluding some users from being able to utilize these functions due to height and/or length restrictions in their artificial limbs. In addition, multiple components increased the weight of the structure, which is less desirable for most users. One such structure available to users is the Otto Bock® Delta Twist™ Shock Absorber sold in models 4R120 and 4R121=30.

The vacuum pump of the present invention also provides for controlled rotation and shock absorption with the pump, so as to reduce the number of components within the artificial limb structure. The rotational structure, as shown best in FIGS. 12 and 13, includes a pair of sliders 231 positioned within an inner diameter of the base 230. Each slider 231 includes a pair of mounting slots 232 that allow for a limited range of sliding movement of the slider 231. Removably mounted adjacent the pair of sliders 231 are two elastomer plates 233 formed from a resilient elastomeric material having a desired durometer or hardness or stiffness. These elastomer plates 233 may have the same stiffness or a different stiffness. In addition, the elastomer plates 233 may be exchanged for plates of a different stiffness, as desired by the user. Positioned between the two elastomer plates 233 is a base stud 234 secured to the inner diameter of the base 230.

The rotational structure also includes a shaft stud 217 secured to the shaft 210. When the shaft 210 is inserted into the base 230, the shaft stud 217 is positioned to be inserted between the pair of sliders 231 in gap 235. In operation, when the shaft 210 rotates, the shaft stud 217 pushes against one of the sliders 231 which, in turn, slides toward and engages one of the elastomer plates 233. The elastomer plate 233 is then deformed by compression between the slider 231 and the base stud 234. The shaft stud 217 is free to slide between the pair of sliders 231 during extension and return of the shaft 210. Alternatively, instead of elastomer plates that are deformed by compression, other resilient components may be provided that are deformed by other means, such as extension or bending.

The shock absorption structure of the vacuum pump 200 includes an spring element 250 and a pneumatic spring 260. The spring element 250 preferably has a generally linear increase in resistance as it is compressed. In one embodiment, the spring element 250 comprises an elastomeric material. The elastomeric material is relatively damp and thus limits the shaft extension rate, thereby limiting the rebound of the shaft 210 upon release of compressive force on the springs 250, 260. In this embodiment, the spring element 250 includes a elastomeric rod 251 that may be provided in different durometers depending on the needs of the user. This rod 251 may also be exchanged with a different durometer rod as the user's needs change.

A first end 252 of the rod 251 is positioned within a elastomer cup 254. A second end 253 of the rod 251 is positioned against an inner upper surface 241 of the cap 240. The elastomer cup 254 is threaded into the inner diameter of the shaft 210 until the rod 251 is suitably compressed against the cap surface 241. The more the cup 254 is threaded into the shaft 210, the greater the preload is on the rod 251. Other means for exerting preload on the rod 251 may be provided.

The pneumatic spring 260 operates at the internal end of the shaft 210 and includes a pneumatic spring or shock absorption chamber 224. A pneumatic spring has a generally exponential stiffness increase as it is compressed. It provides the user with a relatively easily accessible method of temporarily increasing the compressive stiffness of the pump 200 for athletic activities, and also provides a bottoming resistance due to the non-linear stiffness characteristics. The pressure of the pneumatic spring 260 can be increased by pumping air into the shock absorption chamber 224 through an air valve 262. In this embodiment, the air valve 262 is a Schraeder type valve similar to those provided on bicycle tires and the like. However, other types of air valves are also usable, some of which will be described more below.

Providing two different spring structures for the vacuum pump 200 also allows for redundancy within the shock absorption system. This generally increases the reliability of the pump 200, since it is possible to operate the pump 200 using only one of the spring types 250, 260 should a malfunction occur in the other spring.

As shown in FIGS. 19-29, a second embodiment of a vacuum pump 300 in accordance with the present invention includes a shaft 310 and a housing 320. The housing 320 includes a base 330 and a cap 340. At a first end 301 of the pump 300, the shaft 310 includes an integral coupler 312 formed as a tube clamp. In one embodiment, the tube clamp is sized for 30 mm tubes, a common prosthetic industry component. In addition to the tube clamp of coupler 312 and the receiver of coupler 212, other types of attachment configurations, now known or later utilized in the prosthetic industry, formed integrally with a shaft or added to the shaft may also be provided, and are within the scope of the present invention.

At an opposite end 302 of the pump 300, the housing 320 at cap 340 includes a integrally formed prosthetic pyramid connector 305. Inclusion of the connector 305 integral with the pump housing 320 saves height and weight. In addition, it may provide a cost savings because a practitioner selling, distributing, or supplying the pump 300 does not need to purchase and attach a separate attachment component.

The internal components of the pump 300 are basically the same as the components of the first embodiment vacuum pump 200 described above. Therefore, all of the corresponding parts will not be described again. However, the differing parts are highlighted below.

As with the first embodiment, the vacuum pump 300 includes internal chambers for vacuum production and shock absorption. An intake valve 325 and an exhaust valve 326 both fluidly connect to the vacuum chamber to facilitate formation of the vacuum in a socket or other enclosure to which the pump 300 is attached. A piston 316 is coupled to the shaft 310 and rides within the housing 320 in the vacuum chamber. As with the prior embodiment, a plurality of X-rings 304 and O-rings 303 are provided for sealing the chambers of the pump 300. In this embodiment, however, each X-ring 304 is positioned adjacent to a backup ring 306, as shown in detail in FIGS. 23, 24 and 26. Backup rings are provided to stabilize the X-rings and restrict extrusion of a seal into the clearance gap between moving parts.

In this embodiment, the access port to the pneumatic spring or shock absorber chamber is a flush, athletic valve, similar to those provided on sport balls, such as soccer balls and basket balls. A resilient valve member 367 is sandwiched between a nut 366 and a mounting member 368 within the cap 340. An orifice 369 fluidly connects the exterior of the pump 300 to the shock absorber chamber. A pump needle commonly used to inflate a ball or other object may be inserted through the orifice 369 to add air to the chamber, as needed in a manner described above. The provision of a flush valve, instead of a valve that protrudes from the pump, generally reduces the possibility of valve damage due to impact by external objects. In addition, it is less likely to catch on clothing, tubing, or other prosthetic or personal items.

This second embodiment of a pump 300 is even smaller and more light weight than the first embodiment. It is preferably formed from coated or finished aluminum in order to minimize the weight. When so configured, it is primarily suitable for lighter weight applications, but may be configured with stronger and heavier components for heavier duty situations.

As shown in FIGS. 28-32, a third embodiment of a vacuum pump 400 in accordance with the present invention includes a shaft 410 and a housing 420. The housing 420 includes a base 430 and a cap 440, similar to the previously described embodiments. In this embodiment, the cap 440 is configured with a standard four-hole bolt pattern 405, similar to pattern 205 shown in the first embodiment. This allows for attachment to a variety of prosthetic connectors, as are known in the art. Alternatively, other types of attachment devices and/or methods may also be employed.

At the opposite end of the pump 400, the shaft 410 includes an integral coupler 412 formed as a receiver for receiving a prosthetic pyramid connector or other suitable connector. However, other types of connectors, both integrally formed and separately attached, are usable.

The vacuum pump 400 of this embodiment includes the same or similar internal components as those described above for either the first and/or second embodiments, and thus the details will not be repeated. In this embodiment, the pump 400 is shown to include the athletic flush valve 465, which is beneficial for the user for the reasons set forth above. Pump 400 also includes X-rings 404 as seals with backup rings 406 for improved wear resistance and functionality.

The vacuum pump 400 is preferably formed from stainless steel components for heavier duty use. However, some components may be formed from coated or finished aluminum, or other suitable materials, as needed to provide the desired strength, durability and weight.

Figure 33:
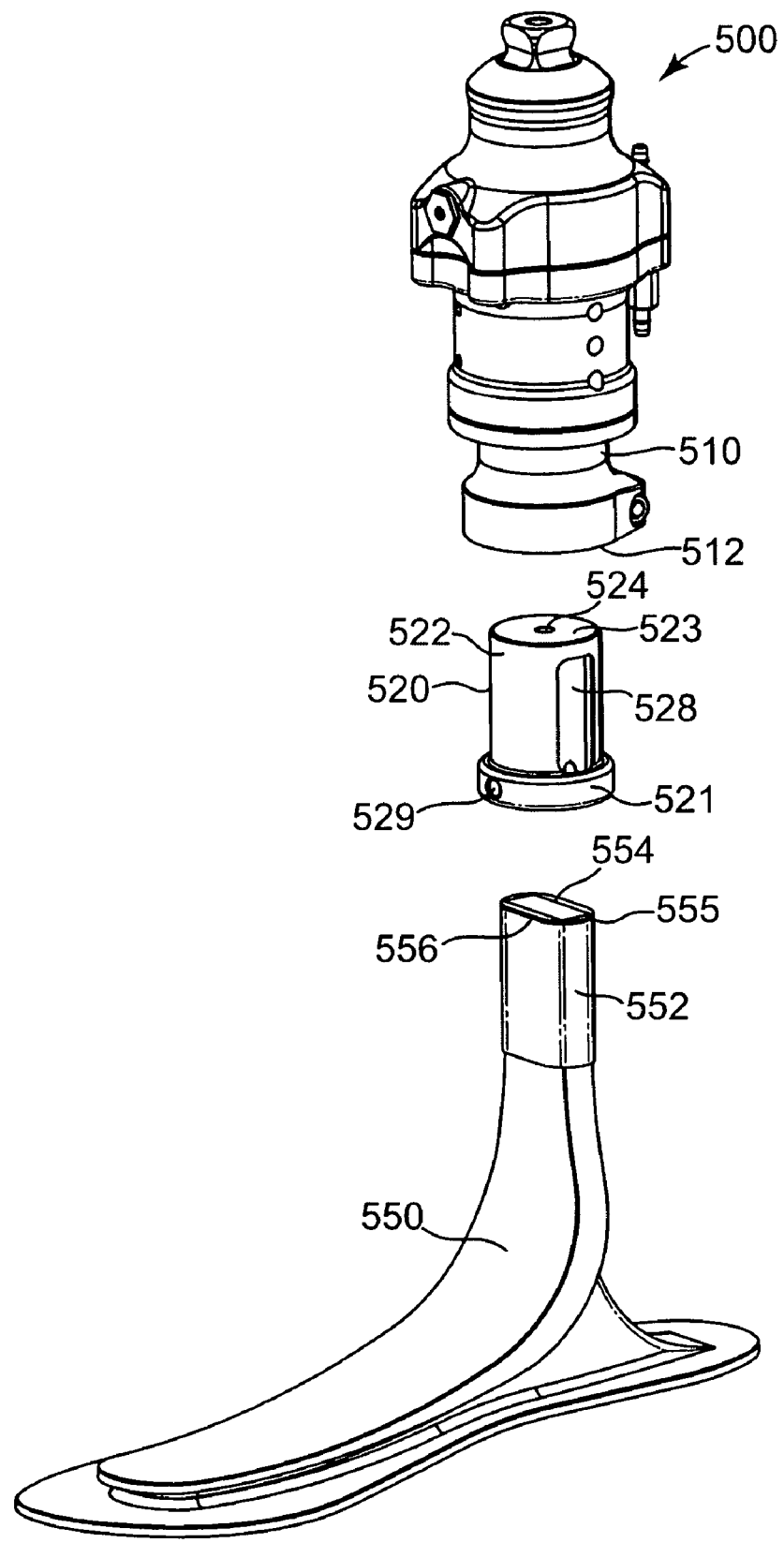
FIG. 33 is an exploded perspective view of a fourth embodiment of a pump in accordance with the present invention, an adapter and an integral pylon-style prosthetic foot.
Figure 34:
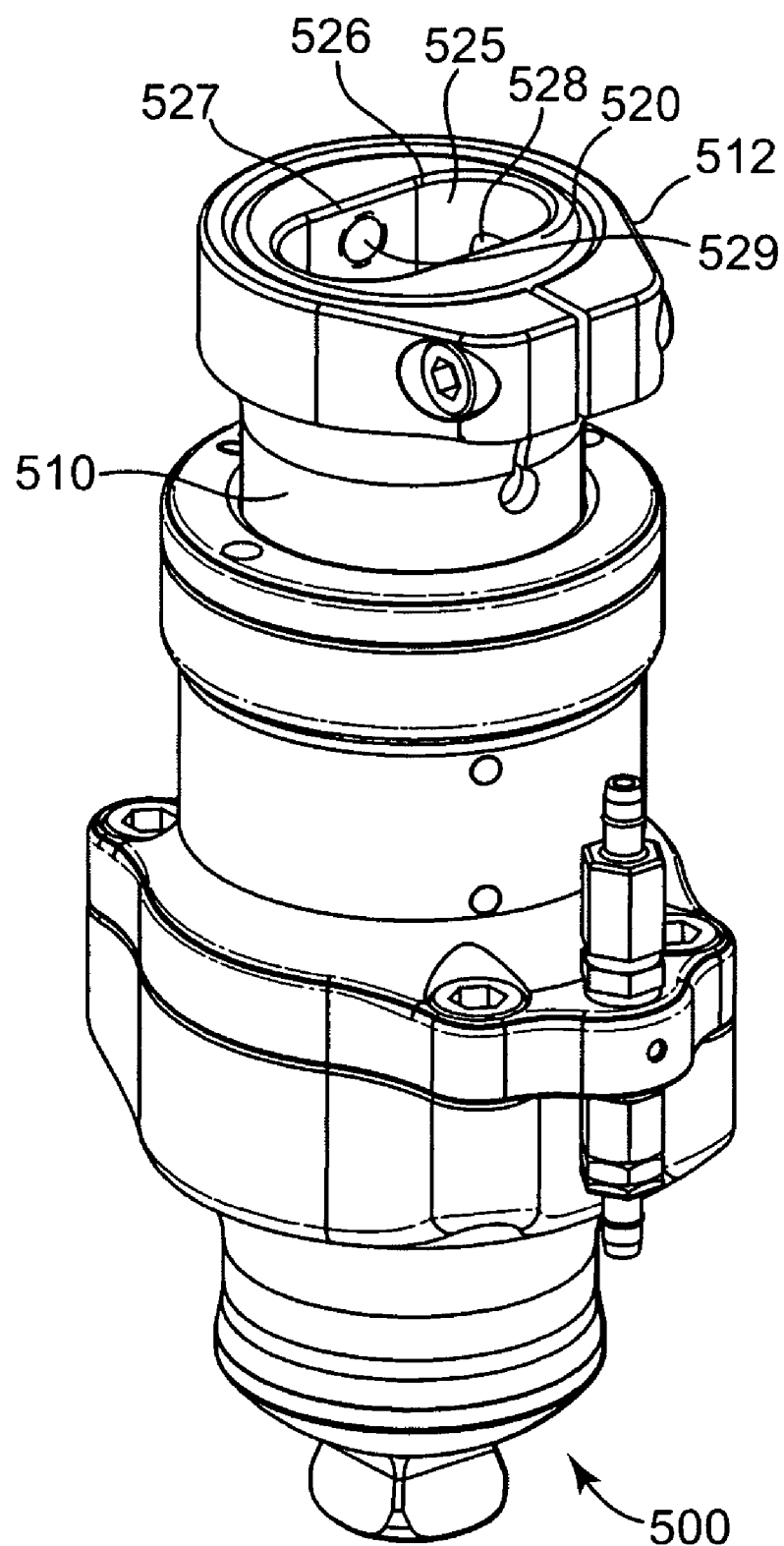
FIG. 34 is a perspective bottom view of the pump of FIG. 33, including the adapter.
Figure 35:
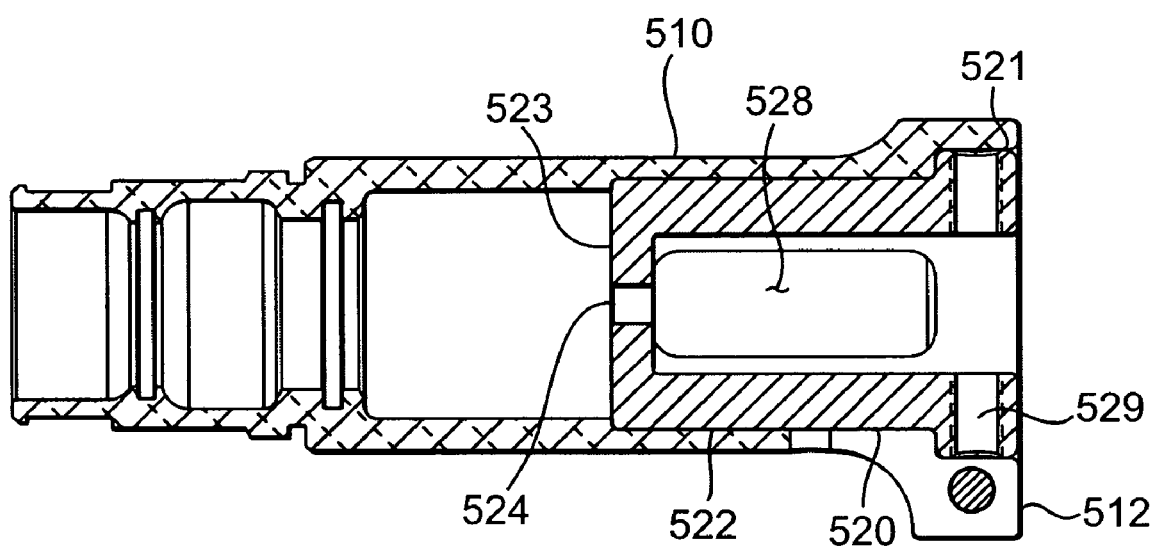
FIG. 35 is a cross-sectional side view of a pump shaft with the adapter of FIGS. 34 and 35 positioned within the shaft.

Referring now to FIGS. 33-35, a fourth embodiment of a vacuum pump in accordance with the present invention is shown adapted for attachment to an integral pylon-style prosthetic foot. In FIG. 33, a prosthetic foot 550 includes a generally, vertically oriented integral pylon 552 having an external profile 554. The profile 554 is shown as being generally oblong, having curved ends 555 and elongated straight sides 556. However, other profiles are also possible, including profiles that are oval, elliptical, rectangular or other suitable shapes. By integral pylon, it is meant that a pylon-type structure is formed in conjunction with a portion of the foot and/or ankle structure.

The vacuum pump 500 of this embodiment is shown to be similar to pump 300 of the second embodiment and includes the same or similar internal and external components as those described above for any of the embodiments, such that the components may be mixed and matched as needed. However, in this embodiment, the shaft 510 includes an integral coupler 512 formed as a tube clamp. In addition, the vacuum pump 500 includes a pylon adapter 520 sized and shaped to be received within the shaft 510 and secured by or fastened to the tube clamp 512.

The pylon adapter 520 includes an exterior configuration designed to generally correspond to the interior configuration of the shaft 510. In this embodiment, the pylon adapter 520 includes a generally cylindrical mounting ring 521 attached to a generally cylindrical component 522 having a smaller diameter than the ring 521. The tube clamp 512 secures or fastens the adapter 520 within the shaft 510 about the mounting ring 521. However, other means for securing or fastening the adapter 520 within the shaft 510 may be provided.

A bore 525 is formed within the ring 521 and the cylindrical component 522, with the bore 525 shaped to correspond to the integral pylon profile 554. In this embodiment, the bore 525 is formed with curved ends 526 and generally straight, elongated sides 527. An air passage aperture 524 is provided through an end 523 of the component 521 into the bore 525. The cylindrical component 522 further includes a pair of oblong openings 528 formed through walls of the cylindrical component 521 into the bore 525. A pair of set screws 529 extend on opposite sides of the ring 521 through to the bore 525. However, other means of fastening or securing the pylon 552 may be provided.

In operation, the adapter is placed onto the pylon 552 of a foot 550 with the bore 525 receiving the pylon 552 in a relatively tight, but slideable fit. The air passage 524 and oblong openings 528 allow for expulsion of air within the bore 525 as the pylon 552 is slid into the adapter 520. The set screws 529 are then used to secure or fasten the adapter 520 to the pylon 552. The pylon/adapter combination is then inserted into the shaft 510 and secured or fastened to the shaft 510 by the tube clamp 512 or other suitable coupler. Alternatively, the adapter 520 may be inserted into and secured or fastened to the shaft 510 prior to insertion of the pylon 552 into the adapter 520.

Optionally, the adapter 520 may be formed within the shaft 510 as an integral portion of the shaft 510. In such as case, different shafts 510 could be provided having bores 525 corresponding to different pylon profiles 554, such that a vacuum pump 500 could be customized for a particular use. Alternatively, a suitable adapter 520 having a desired bore 525 could be permanently mounted within an available shaft 510.

The adapter 520 of the present embodiment allows for effective mounting of the vacuum pump 500 onto an integral pylon-style prosthetic foot 550 without the need for multiple couplers and components, as were historically required. As a result, the vacuum pump and foot combination tends to be more compact and, thus, usable in situations where height is an issue. It is also generally less expensive than the multiple fitting and/or component version. The provision of a removable adapter 520 also helps alleviate the need to stock multiple shafts 510 or custom make a pump 500 to fit a particular user's requirements. Instead, a suitable adapter 520 may be provided and secured within a standard vacuum pump 500, thus allowing for flexibility and changeablility as the user's desires and needs change.

In some cases, an integral pylon prosthetic foot for use in an artificial limb is preferred due to performance requirements of the amputee. However, the distance between the foot and a socket of the artificial limb is limited. In these situations, use of a vacuum pump and shock absorber in-line with the socket and pylon may be difficult due to the height restrictions. Use of the adapter and pump configuration of the present embodiment provides a more compact pump configuration for use with the integral pylon foot, thus enabling more users to take advantage of the vacuum enhanced socket system described above.

Figure 36:
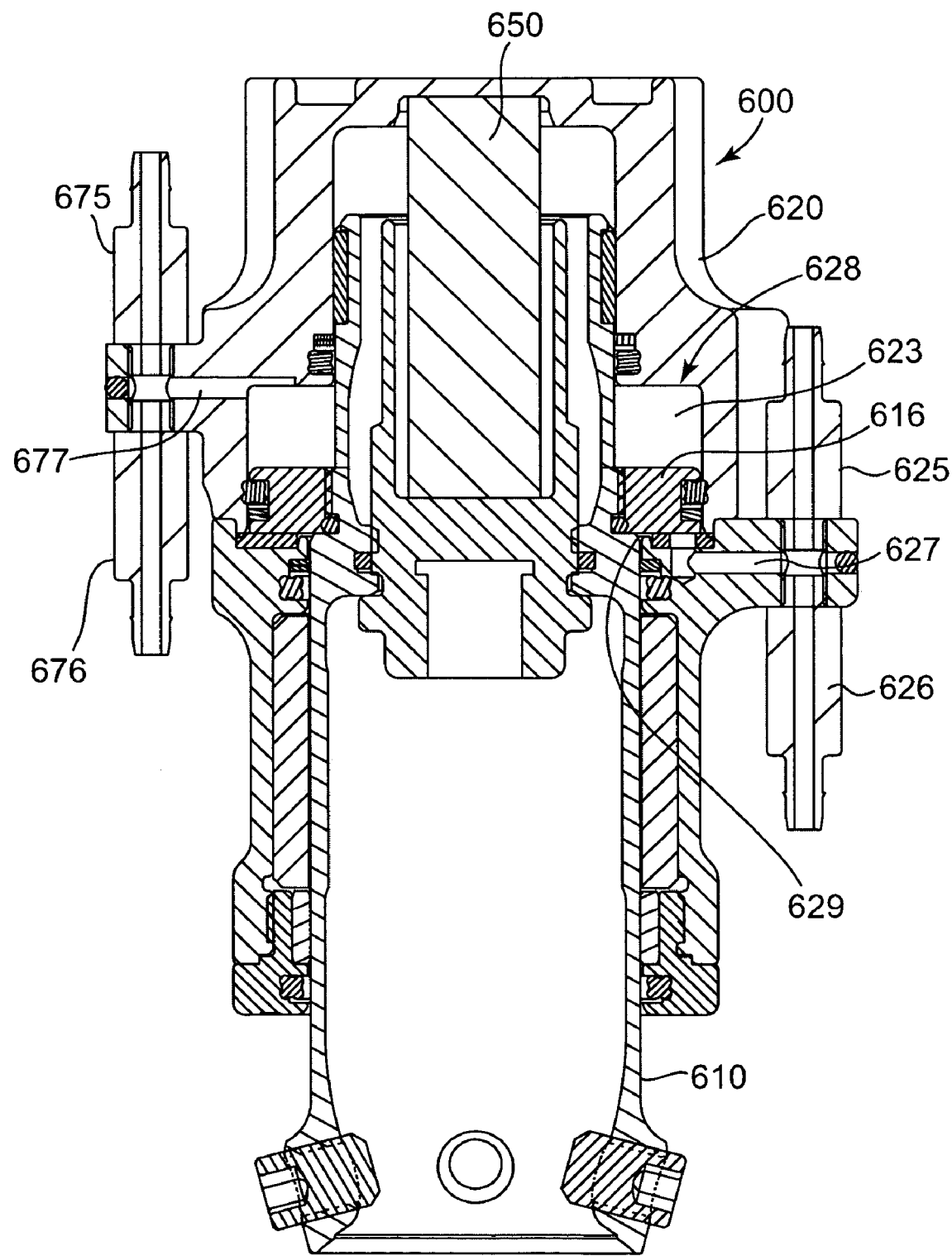
FIG. 36 is a cross-sectional side view of a fifth embodiment of a pump in accordance with the present invention.

Another alternative to the embodiments described above, or fifth embodiment, is the replacement of the pneumatic spring with a second vacuum pump configuration. In FIG. 36, a pump 600, which is similar to pump 200 shown in FIGS. 4-18, is shown having a housing 620 and shaft 610. In this embodiment, a vacuum or pump chamber 623 is formed between the shaft 610 and the housing 620, and a piston 616 mounted to the shaft 610 reciprocates within the vacuum chamber 623. As with pump 200, an intake valve 625 is mounted to the housing 620 and is provided in fluid communication with the vacuum chamber 623 by a communication passage 627 on the bottom or pylon side 629 of the vacuum chamber 623. This intake valve 625 is configured for fluid connection to a socket of the artificial limb, such as socket 102. An exhaust valve 626 is also provided in fluid communication with the vacuum chamber 623 at passage 627.

In this embodiment, a second intake valve 675 is mounted to the housing 620 and is provided in fluid communication with the vacuum chamber 623 by a communication passage 677. This second communication passage 677 is provided on the top or socket side 628 of the vacuum chamber 623. A second exhaust valve 676 is also provided in fluid communication with the vacuum chamber 623 at passage 677.

Upon upward/inward stroke of the piston 616 within the vacuum chamber 623, air in the top side 628 of the vacuum chamber 623 is expelled through the exhaust valve 626. In addition, air from a connected socket, such as socket 102, is pulled into the bottom side 629 of the vacuum chamber 623 through the second intake valve 675 and out of the socket, thereby forming a vacuum in the socket. Upon downward/outward stroke of the piston 616, air from the bottom side 629 of the vacuum chamber 623 is expelled through the second exhaust valve 676, while air from the connected socket is pulled into the top side 628 vacuum chamber 623 through the intake valve 625.

This configuration would pump air from the socket on both the extension and compression, or inward and outward stroke, of the shaft 610, thereby doubling the rate at which air is removed from the socket. This configuration includes the installation of a second set of check valves 675, 676 on the socket or proximal side 628 of the piston 616. In addition, an spring element 650 would need to be modified, relative to the spring element 250 described above, to handle the added load produced by elimination of the pneumatic spring 260.

Figure 37:
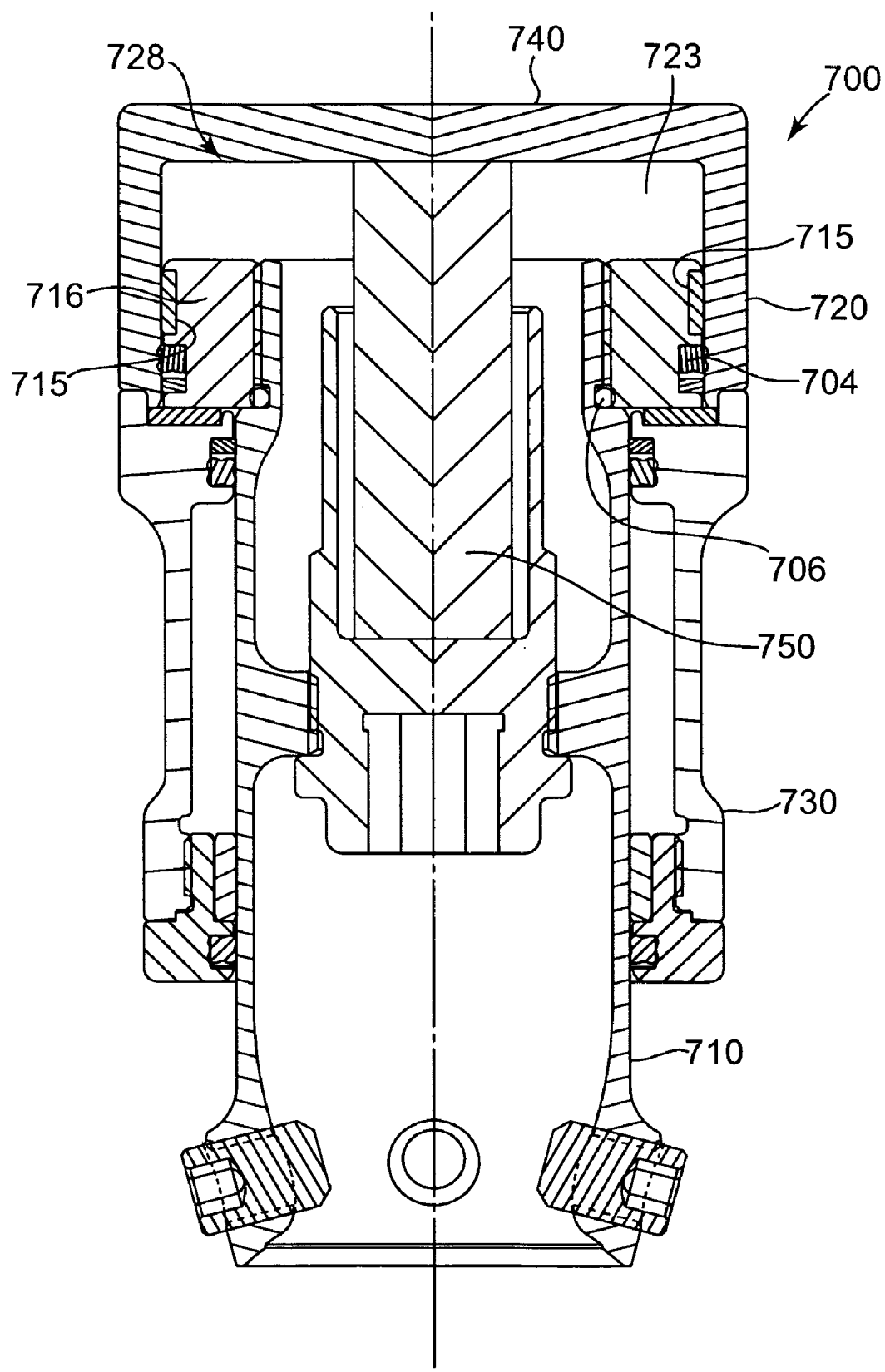
FIG. 37 is a cross-sectional side view of a sixth embodiment of a pump in accordance with the present invention.

A further alternative embodiment, or sixth embodiment, includes placement of the proximal or socket side bearing directly on the piston. In FIG. 37, a pump 700 is shown having a shaft 710 and housing 720, including a base 730 and a cap 740. Between the housing 720 and the shaft 710, a vacuum chamber 723 is formed. In this embodiment, a piston 716 is mounted to the shaft 710 at a top or socket end 728 of the shaft 710. A socket side bearing 715 is mounted on the piston 716 so as to interact with the housing cap 740, in contrast to the above described embodiments wherein the bearings are mounted to a top end of the shaft and not to the piston. Seals 704 are also provided on the piston 716 between the piston 716 and the cap 740, similar to the above described embodiments. An o-ring 706 is provided between the piston 716 and the shaft 710.

In this configuration, the piston 716 is located at the top of the shaft 710 and the shaft 710 does not extend beyond the piston 716. This results in a reduction of the height of the pump 700, such that the height of the housing cap 740 is generally reduced as compared to the previously described embodiments. An spring element 750 may still be provided within the pump 700. However, this configuration also reduces the spacing between the bearings and would require sealing on a wear surface. In addition, no pneumatic spring is provided with this embodiment.

Figure 38:
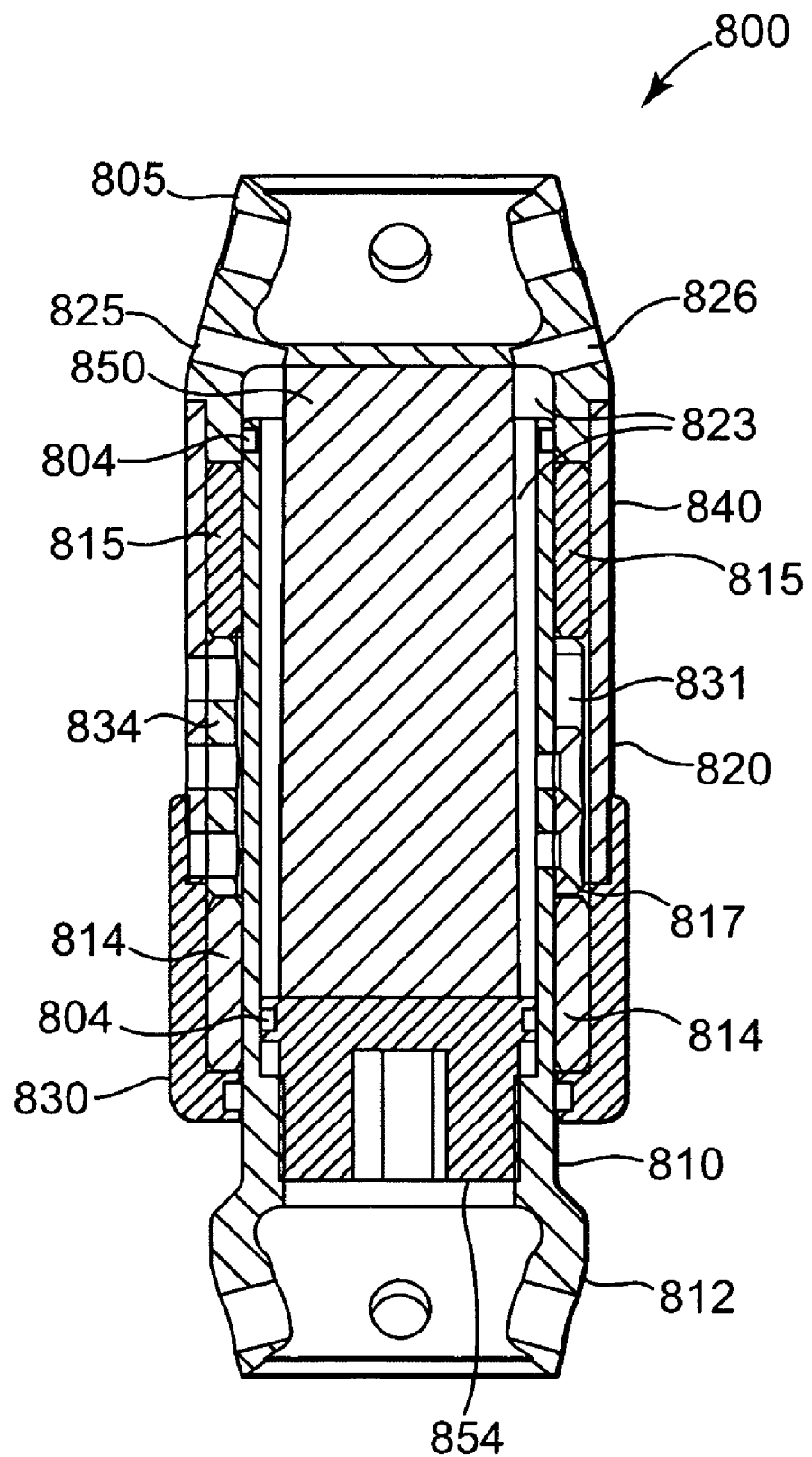
FIG. 38 is a cross-sectional side view of a seventh embodiment of a pump in accordance with the present invention.

Referring now to FIG. 38, a seventh-embodiment is shown as pump 800, including a shaft 810 and a housing 820 having a base 830 and a cap 840. Prosthetic connectors, such as a shaft receiver or pyramid coupler, as described above, are provided to couple the pump 800 to prosthetic components, such as between a socket and a prosthetic foot. As shown, the shaft 810 includes a receiver 812 and the housing 820 includes a receiver 805.

In this embodiment, the pump 800 does not include a piston, but rather the vacuum or pump chamber 823 is formed between the shaft 810 and the housing 820, and within the shaft 810. Multiple seals 804 are provided within the pump 800, as needed to seal the pump chamber 823. Within the shaft 810 and pump chamber 823, a spring element 850 is positioned. In this embodiment, the spring element 850 is a resilient member, such as the elastomeric rods described above. The spring element 850 is placed in compression by a preload adjuster 854, or other means.

A pair of bearings 814, 815 are positioned in the housing 820 adjacent to the shaft 810 to facilitate reciprocation of the shaft 810 within the housing 820. As the shaft 810 moves inward, the spring element 850 compresses further, expanding laterally to substantially fill the pump chamber 823. The more the spring element 850 is compressed, the stiffer it generally becomes, thereby preventing the shaft 810 from bottoming out against the housing 820. Upon release of the inward force, the shaft 810 returns to its original, extended position with respect to the housing 820 and the spring element 850 de-compresses. The reciprocation of the shaft 810 results in the inflow and outflow of air into and out of the pump 800, respectively, in the same or similar manner as described above for the other embodiments.

Within the housing 820 and between the bearings 814, 815, the components for controlled rotation are provided, as described above. In particular, a rotation slider 831, shaft stud 817 and housing stud 834 are shown in FIG. 38. As the shaft 810 rotates with respect to the housing 820, the rotational structure controls the relative rotation.

One advantage of the piston-less pump 800 is the reduced size, cost and weight of the pump. Lower cost, lighter weight and shorter vacuum pumps are needed for the future development of useful, competitive and affordable prosthetic limbs.

Figure 39:
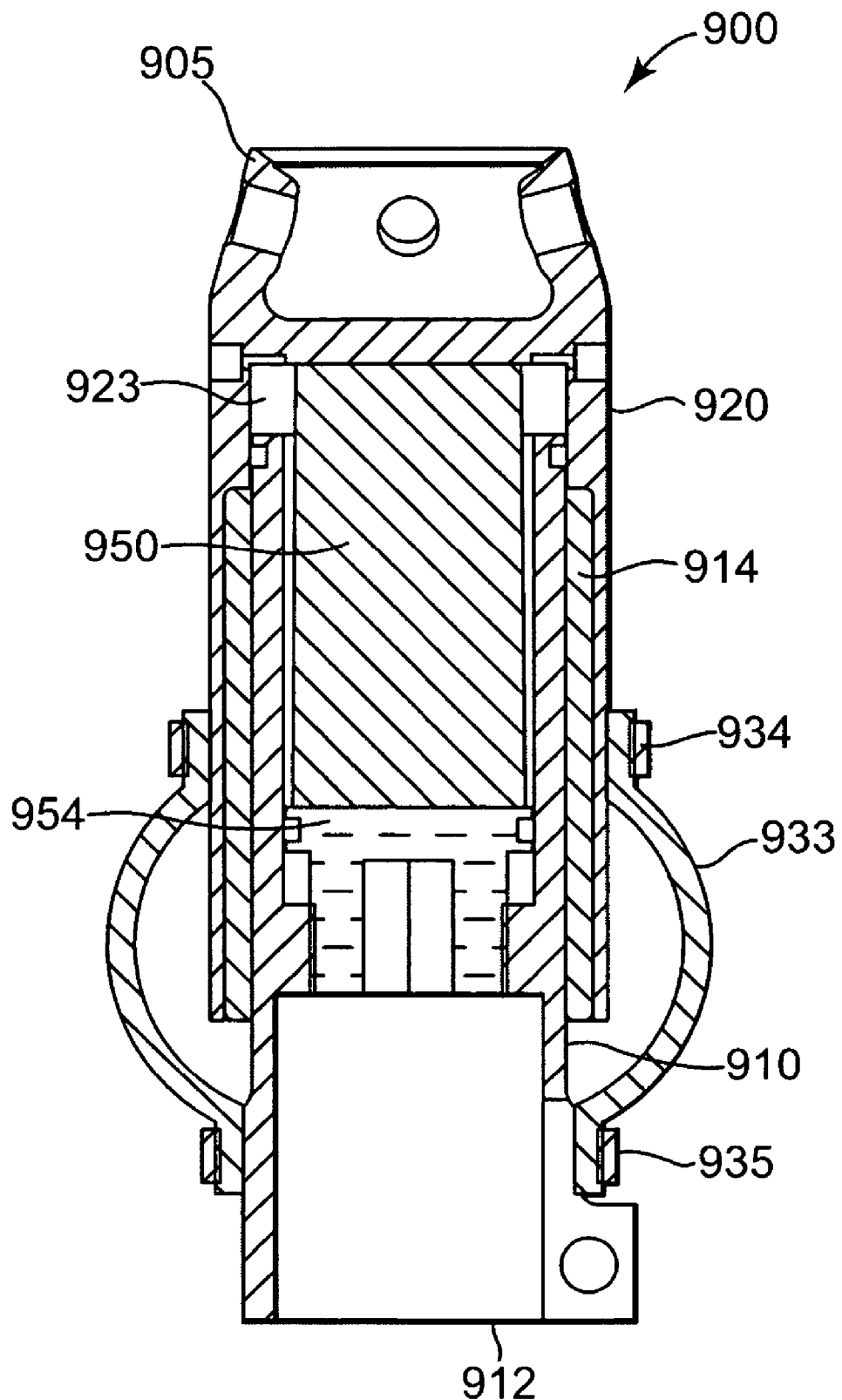
FIG. 39 is a cross-sectional side view of an eighth embodiment of a pump in accordance with the present invention.

An alternative to the internal rotational control structure shown in the above embodiments is shown in FIG. 39. A piston-less pump 900 includes a shaft 910 and a housing 920, with a vacuum or pump chamber 923 formed therebetween. A spring element 950 is positioned within the shaft 910 and pump chamber 923, and can be pre-loaded using a pre-load adjuster 954. Prosthetic device connectors are provided, such as a receiver 905 on the housing 920 and a tube clamp 912 on the shaft. In this embodiment, a single bearing 914 may be used to facilitate shaft reciprocation, instead of the pair of bearings 814, 815, shown in FIG. 38, which are divided by the internal rotational control structure. The bearing 914 is positioned within the housing 920 to surround the shaft 910.

In this embodiment, instead of internal resilient components to control rotation of the shaft, the pump 900 is provided with an external resilient component or sleeve 933. The rotational sleeve 933 is coupled to the housing 920 in a suitable manner, such as by bolts 934 or other means. The sleeve 933 is also coupled to the shaft 910 in a suitable manner, such as by bolts 935 or other means. Other types of connections or coupling methods are also possible and within the scope of the present invention. As the shaft 910 rotates, the rotational sleeve 933 deforms, resisting rotation relative to the housing 920. Other types of shock absorption and rotational control structures are available for use in prosthetic devices, and could be adapted for use in the vacuum pumps of the present invention.

Although the present invention has been described with reference to exemplary embodiments, persons skilled in the art will recognize that changes may be made in form and detail without departing from the spirit and scope of the invention. In addition, the various embodiments described include numerous components which may be provided in various combinations to achieve similar functionality. All such combinations are within the scope of the present invention. Also, various of the components may be eliminated from one or more embodiments to achieve the same function, as described above.

Although shown within respect to a below-the-knee leg residuum, it is also to be understood that the vacuum pumps of the present invention may be used in an above-the-knee leg configuration and/or an upper extremity configuration of an artificial limb.

We claim:

1. A vacuum pump for use with an artificial limb, the vacuum pump comprising:
   a housing couplable to a first prosthetic structure, the housing including a first chamber;
   a shaft couplable to a second prosthetic structure and configured to be received by and to reciprocate within the first chamber, such that the housing and shaft together form a pump chamber;
   an intake port and an exhaust port in fluid communication with the pump chamber;
   a rotational structure configured to control rotation of the shaft with respect to the housing, the rotational structure comprising a movement limiting component mounted internally within the housing and positioned to limit rotational movement of the shaft in both rotational directions and a resilient member positioned such that rotation of the shaft in a first direction results in deformation of the resilient member; and
   a shock absorption structure included within the housing and configured to absorb a shock to the shaft upon movement into the first chamber and provide return of the shaft to an extended position relative to the first chamber,
   wherein movement of the shaft into the first chamber results in expellation of gas out of the pump chamber through the exhaust port, and return of the shaft to the extended position pulls gas into the pump chamber through the intake port, which can create a vacuum in an external component coupled to the pump at the intake valve.

2. The vacuum pump of claim 1, wherein the movement limiting components comprise sliders and wherein the shaft comprises a stud positioned on the shaft between the sliders, such that rotation of the shaft results in contact of the stud against one of sliders so as to move that slider toward and into contact with one of the resilient members.

3. The vacuum pump of claim 1, wherein the resilient members comprise removable elastomeric plates, such that the rotational resilience of the vacuum pump is adjustable by selection of the elastomeric plates.

4. The vacuum pump of claim 1, wherein the shock absorption structure comprises a spring element mounted within the shaft.

5. The vacuum pump of claim 4, wherein the spring element is preloaded to a predetermined level based on requirements of the user.

6. The vacuum pump of claim 4, wherein the spring element comprises an elastomeric rod.

7. The vacuum pump of claim 4, wherein the shock absorption structure further includes a pneumatic spring within the housing, the pneumatic spring including a pneumatic spring chamber positioned between the shaft and housing and filled with gas to a desired level.

8. The vacuum pump of claim 1, wherein the shock absorption structure comprises a pneumatic spring within the housing.

9. The vacuum pump of claim 8, wherein the pneumatic spring comprises a pneumatic spring chamber positioned between the shaft and the housing, with the pneumatic spring chamber filled with gas to a desired level.

10. The vacuum pump of claim 9, wherein the pneumatic spring further comprises a valve coupled to the pneumatic spring chamber, such that the user may input gas into the pneumatic spring chamber as desired via the valve.

11. The vacuum pump of claim 10, wherein the valve comprises a bicycle-type valve.

12. The vacuum pump of claim 8, wherein the shock absorption structure further comprises a mechanical spring element within the shaft.

13. The vacuum pump of claim 1, further comprising a piston coupled to the shaft and positioned within the housing, wherein the pump chamber is formed with respect to the piston, shaft and the housing, such that reciprocation of the shaft results in reciprocation of the piston.

14. A vacuum pump having dual shock absorption for use with an artificial limb, the vacuum pump comprising:
   a housing couplable to a first prosthetic structure, the housing including a base portion at a first end of the housing, a cap portion at a second end of the housing and a first chamber disposed within the housing;
   a shaft couplable to a second prosthetic structure and configured to be received by and to reciprocate within the first chamber, such that the housing and shaft together form a pump chamber, the shaft including a shaft stud, a first bearing disposed between the housing and shaft near the first end and a second bearing disposed between the housing and shaft near the second end, wherein the first and second bearings are positioned on opposing sides of the pump chamber;

a piston coupled to the shaft and positioned within the pump chamber, such that reciprocation of the shaft results in reciprocation of the piston within the pump chamber;

an intake port and an exhaust port in fluid communication with the pump chamber;

a rotational structure mounted internally within the housing, the rotational structure comprising at least one slider component positioned to engage the shaft stud to limit rotational movement of the shaft in both rotational directions and a resilient member positioned to contact the stud such that rotation of the shaft in a first direction results in deformation of the resilient member;

a mechanical spring element within the shaft, the mechanical spring element comprising an elastomeric rod; and a pneumatic spring within the housing and including a pneumatic spring chamber, with the mechanical spring element and pneumatic spring configured to absorb a shock to the shaft upon movement into the first chamber and return of the shaft to an extended position relative to the first chamber, wherein movement of the shaft into the first chamber results in expellation of gas out of the pump chamber through the exhaust port, and return of the shaft to the extended position pulls gas into the pump chamber through the intake port, which can create a vacuum in an external component coupled to the pump at the intake valve.

15. The vacuum pump of claim 14, wherein the mechanical spring element is preloaded to a desired level by a preload member.

16. The vacuum pump of claim 15, wherein the preload member includes an elastomeric cap that is adjustable to apply the preload at a desired level.

17. The vacuum pump of claim 14, wherein the pneumatic spring further comprises a valve coupled to the pneumatic spring chamber, such that the user may input gas into the pneumatic spring chamber as desired via the valve.

18. The vacuum pump of claim 17, wherein the valve comprises a bicycle valve.

19. The vacuum pump of claim 14, wherein the rotational structure comprises a pair of sliders mounted within the housing, a pair of resilient plates mounted within the housing adjacent to the pair of sliders and a stud mounted to the shaft and positioned between the pair of sliders, such that rotation of the shaft in a first direction results in movement of the stud against one of the pair of sliders, which slides in the direction of rotation until it contacts one of the pair of resilient plates, the resilient plate then deforming upon further rotation of the shaft.

20. The vacuum pump of claim 14, further comprising intake and exhaust valves fluidly coupled to the intake and exhaust ports, respectively.

21. The vacuum pump of claim 20, wherein the intake and exhaust valves comprise one-way check valves.

* * * * *